United States Patent
Huth et al.

(10) Patent No.: US 9,681,802 B2
(45) Date of Patent: Jun. 20, 2017

(54) FAST ABSOLUTE-REFLECTANCE METHOD FOR THE DETERMINATION OF TEAR FILM LIPID LAYER THICKNESS

(71) Applicant: ABBOTT MEDICAL OPTICS INC., Santa Ana, CA (US)

(72) Inventors: Stanley W. Huth, Newport Beach, CA (US); Denise Tran, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 14/831,678

(22) Filed: Aug. 20, 2015

(65) Prior Publication Data

US 2015/0351628 A1    Dec. 10, 2015

Related U.S. Application Data

(63) Continuation-in-part of application No. 14/298,176, filed on Jun. 6, 2014, and a continuation-in-part of application No. 14/298,036, filed on Jun. 6, 2014, now Pat. No. 9,456,741.

(51) Int. Cl.
*A61B 3/10* (2006.01)
*A61B 3/00* (2006.01)
*G01J 3/45* (2006.01)

(52) U.S. Cl.
CPC ............ *A61B 3/101* (2013.01); *A61B 3/0025* (2013.01); *A61B 3/1005* (2013.01); *G01J 3/45* (2013.01)

(58) Field of Classification Search
CPC ........ A61B 3/1005; A61B 3/101; A61B 3/107
USPC ...................................... 351/205, 212, 246
See application file for complete search history.

(56) References Cited

U.S. PATENT DOCUMENTS

| | | |
|---|---|---|
| 5,045,704 A | 9/1991 | Coates |
| 6,236,459 B1 | 5/2001 | Negahdaripour et al. |
| 6,916,096 B2 | 7/2005 | Eberl et al. |
| 7,281,801 B2 | 10/2007 | Wang |
| 7,758,190 B2 | 7/2010 | Korb et al. |
| 7,866,819 B2 | 1/2011 | Tuan |
| 7,963,522 B2 | 6/2011 | Hoover |

(Continued)

FOREIGN PATENT DOCUMENTS

WO    2013163367 A1    10/2013

OTHER PUBLICATIONS

Bosch S., et al., "A Method for the Measurement of Reflectances of Spherical Surfaces," Measurement Science and Technology, 1993, vol. 4 (2), pp. 190-192.

(Continued)

*Primary Examiner* — Jack Dinh
(74) *Attorney, Agent, or Firm* — Abbott Medical Optics Inc.

(57) ABSTRACT

A method for determining reflectivity of a tear film lipid layer of a patient and recommending a course of treatment based on the same. The method includes the steps of: measuring a tear film aqueous plus lipid layer relative reflectance spectrum using a wavelength-dependent optical interferometer; converting the measured tear film aqueous plus lipid layer relative reflectance spectrum to a calculated absolute reflectance spectrum; comparing the calculated absolute reflectance spectrum to a theoretical absolute lipid reflectance spectrum to determine a tear film lipid layer thickness; and determining a reflectivity value for the tear film lipid layer thickness at a first wavelength of light corresponding to ultraviolet, violet, or blue light.

32 Claims, 15 Drawing Sheets

(56) References Cited

U.S. PATENT DOCUMENTS

| | | | |
|---|---|---|---|
| 8,192,026 | B2 | 6/2012 | Gravely et al. |
| 8,585,204 | B2 | 11/2013 | Korb et al. |
| 8,591,033 | B2 | 11/2013 | Korb et al. |
| 8,602,557 | B2 | 12/2013 | Huth et al. |
| 2004/0212781 | A1 | 10/2004 | Mihashi et al. |
| 2006/0109423 | A1 | 5/2006 | Wang |
| 2007/0174014 | A1 | 7/2007 | Halm |
| 2007/0215801 | A1 | 9/2007 | Walsh et al. |
| 2008/0273171 | A1 | 11/2008 | Huth et al. |
| 2009/0201465 | A1 | 8/2009 | Huth |
| 2010/0253907 | A1 | 10/2010 | Korb et al. |
| 2013/0141698 | A1 | 6/2013 | Huth et al. |
| 2013/0169933 | A1 | 7/2013 | Wang |
| 2013/0229624 | A1 | 9/2013 | Korb et al. |
| 2013/0293842 | A1 | 11/2013 | Grenon et al. |
| 2014/0104574 | A1 | 4/2014 | Grenon et al. |
| 2014/0118699 | A1 | 5/2014 | Huth et al. |

OTHER PUBLICATIONS

Fogt N., et al., "Interferometric Measurement of Tear Film Thickness by Use of Spectral Oscillations," Journal of Optical Society of America, 1998, vol. 15 (1), pp. 268-275.

Gardner et al., "Tear Film Thickness: Responsiveness to Potential Cognitive Demands", American Academy of Optometry, Tampa Dec. 2004, 1 page.

Geldis et al., "The Impact of Punctual Occulsion on Soft Contact Lends Wearing Comfort and the Tear Film," Eye and Contact Lens, pp. 261-265, 2008, vol. 34 (5).

Goto E., et al., "Computer-Synthesis of an Interference Color Chart of Human Tear Lipid Layer, by a Colorimetric Approach," Investigative Ophthalmology and Visual Science, 2003, vol. 44 (11), pp. 4693-4697.

Goto E., et al., "Differentiation of Lipid Tear Deficiency Dry Eye by Kinetic Analysis of Tear Interference Images," Archives of Ophthalmology, 2003, vol. 121 (2), pp. 173-180.

Hinel E., et al., "Concurrent interferometric Measures of Lipid Layer Thickness and Tear Film Thinning Before and After Application of Lipid Emulsion Drop", American Academy of Optometry, Anaheim Oct. 2008, 1 page.

International Preliminary Report on Patentability and Written Opinion for Application No. PCT/US08/062682, mailed on Nov. 10, 2009, 12 pages.

International Search Report and Written Opinion for Application No. PCT/US2015/030392, mailed on Oct. 5, 2015, 12 pages.

International Search Report for Application No. PCT/US08/062682, mailed on Nov. 5, 2008, 6 pages.

International Search Report for Application No. PCT/US2015/030385, mailed on Jul. 27, 2015, 3 pages.

Kimball et al., Evaporation is the Primary Mechanism of Pre-Corneal Tear Film Thinning. [online], Oct. 2008 [retieved on Feb. 25, 2009]. Retrieved from the Internet.

Kimball et al., Improving Interferometric Tear Thickness Measurements by Using Longer Wavelengths. [online], [retrieved on Feb. 25, 2009]. Retrieved from the Internet.

King S., et al., "Three Interferometric Methods for Measuring the Thickness of Layers of the Tear Film," Optometry and Vision Science, 1999, vol. 76 (1), pp. 19-32.

King S., et al., "Why does Dry Eye Affect Inferior Cornea More than Superior Cornea", American Academy of Optometry, 2002, pp. 1-2.

King-Smith et al., "In vivo Measurement of the Thickness of Human Corneal Endothelium and Descemets Membrane Using Interferometry, E-Abstract 157," Investigative Ophthalmology & Visual Science, 2002, vol. 43.

King-Smith. et. al., "Noninvasive Measurement of the Thickness of the Human Corneal Endothelium and Descemet's Membrane", American Academy of Optometry, Dec. 8, 2001, pp. 1-2.

King-Smith et al., "Roughness of the Corneal Surface by Interferometry", Association for Research in Vision and Ophthalmology, May 6, 2007, 1 page.

King-Smith et al., "The Thickness of the Human Precorneal Tear Film: Evidence from Reflection Spectra," Investigative & Visual Science, pp. 3348-3359, 2000, vol. 41 (11).

King-Smith et al., "The Thickness of the Tear Film," Current Eye Research, pp. 357-368, 2004, vol. 29 (4-5), Taylor & Francis Health Sciences.

King-Smith P., et al., Interferometric Analysis of Reflections from the Tear Film and Ocular Surface. [online], [retrieved on Feb. 25, 2009]. Retrieved from the Internet.

King-Smith P., et al., "Measurement of the Thickness of the Lipid Layer of the Tear Film Using Reflection Spectra," Association for Research in Vision and Ophthalmology, Inc., 2008, Grand Floridian A, Program 1540.

King-Smith P.E., et al., "A Tear Layer of Thickness 1.6 to 7.3 Micrometer Determined from Reflectance Spectra," Investigative Ophthalmology & Visual Science, 1998, vol. 39 (4), pp. 2446-B303.

King-Smith P.E., et al., "Can the Mucus Layer of the Tear Film be Deomstrated by Interferometry", Investigative Ophthalmology & Visual Science, 2004, vol. 45, pp. 1-2.

King-Smith P.E., et al., "Further Evidence that the Thickness of the Normal Human Tear Film is about 3 Micrometre," Investigative Ophthalmology & Visual Science, 2000, vol. 41 (4), pp. 337-B337.

King-Smith P.E., et al., "Interferometric Imaging of the Full Thickness of the Precorneal Tear Film," Journal of the Optical Society of America A, Optics, Image Science, and Vision, 2006, vol. 23 (9), pp. 2097-2104.

King-Smith P.E., et al., "Is the Thickness of the Tear Film About 40 Micrometre or About 3 Micrometre", Investigative Ophthalmology & Visual Science, 1999, vol. 40 (4), pp. 2876-B751.

King-Smith P.E., et al., "Measurement of Tear Film Thickness by Spectro-Photometry," Investigative Ophthalmology & Visual Science, 1996, vol. 37 (3), pp. 4984-B594.

King-Smith P.,et al., "Is Inferior Tear Film Thinner than Superior Tear Film", Investigative Ophthalmology & Visual Science, 2003, vol. 44, pp. 2476.

Korb D.R., et al., "Tear Film Lipid Layer Thickness as a Function of Blinking," Cornea, 1994, vol. 13 (4), pp. 354-359.

Korb D.R., et al., "The Effect of Two Novel Lubricant Eye Drops on Tear Film Lipid Layer Thickness in Subjects With Dry Eye Symptoms," Optometry and Vision Science, 2005, vol. 82 (7), pp. 494-601.

Nichols, et al., "Assessing Visual Parameters in Dry Eye Disease," Cornea and Contact Lens, [retrieved on Feb. 25, 2009]. Retrieved from the Internet.

Nichols et al., "Lipid Layer Thickness and Tear Film Thinning Before and After Application of a Lipid Emulsion Drop,," Association for Research in Vision and Ophthalmoogy, 2008.

Nichols et al., "Tear Film Thickness and Thinning Rate Following a Six-Week Trial of 2% Diquafosol Tetrasodium vs. Placebo in Dry Eye Patients," 2006.

Nichols et al., "The Impact of Contact Lens Care Solutions on the Thickness of the Tear Film and Contact Lens," Cornea, Clinical Sciences, pp. 825-832, 2005, vol. 24 (7).

Nichols J.J. et al., "Hydrogel Contact Lens Binding Induced by Contact Lens Rewetting Drops," Optometry and Vision Science, 2008, vol. 85(4), pp. 236-240.

Nichols J.J., et al., "Thickness of the Pre- and Post-Contact Lens Tear Film Measured In Vivo by Interferometry," Investigative Ophthalmology & Visual Science, 2003, vol. 44 (1), pp. 68-77.

Nichols J.J., et al., "Thinning Rate of the Precorneal and Prelens Tear Films," Investigative Ophthalmology & Visual Science, 2005, vol. 46 (7), pp. 2353-2361.

Nicols et al, "Role of Lipid Layer as a Barrier to Pre-Lens Tear Film Thinning", American Academy of Optometry, Anaheim Oct. 25, 2008, 1 page.

Scaffidi R.C., et al., "Comparison of the Efficacy of Two Lipid Emulsion Eyedrops in Increasing Tear Film Lipid Layer Thickness," Eye Contact Lens, 2007, vol. 33 (1), pp. 38-44.

Schlote T., et al., "Marked Reduction and Distinct Patterns of Eye Blinking in Patients With Moderately Dry Eyes During Video Display Terminal Use," Graefe's Archive for Clinical and Experimental Ophthalmology, 2004, vol. 242 (4), pp. 306-312.

(56) References Cited

OTHER PUBLICATIONS

Schott BK7 Refractive Index Reference, Which is Equivalent to and Replaces Schott Technical Information Document TIE-29, 2005, 17 pages, retrieved from Internet.
Stenzel O., "The Physics of Thin Film Optical Spectra: An Introduction," in: Springer Series in Surface Sciences, 2005, vol. 44, Ertl G., Eds., Springer-Verlag Berlin Heidelberg, pp. 71-98.
Tiffany J.M., et al., "Refractive Index of Meibomian and Other Lipids," Current Eye Research, 1986, vol. 5 (11), pp. 887-889.
Yap M., "Tear Break-up Time is Related to Blink Frequency," Acta Ophthalmologica, 1991, vol. 69 (1), pp. 92-94.
Zhu H., et al., "A Mathematical Model for Ocular Tear and Solute Balance," Current Eye Research, 2005, vol. 30 (10), pp. 841-854.

FAST ABSOLUTE-REFLECTANCE METHOD FOR THE DETERMINATION OF TEAR FILM LIPID LAYER THICKNESS

CROSS-REFERENCE TO RELATED APPLICATIONS

The present application is a continuation-in-part and claims priority to U.S. patent application Ser. No. 14/298,176, filed Jun. 6, 2014, and Ser. No. 14/298,036, filed Jun. 6, 2014, which are incorporated herein by reference in its entirety.

BACKGROUND

The present invention relates to determination of tear film lipid layer thickness.

Dry eye disease is most often caused by excessive tear film evaporation, leading to hyperosmolarity of the tear film, resulting in ocular surface inflammation and exacerbation of the problem. Excessive tear film evaporation is often caused by an abnormal tear film lipid layer, either in amount or in quality. The amount or quality of tear film lipid can manifest itself in changes in thickness of the lipid layer. Generally, a thicker lipid layer is associated with a normal tear film, whereas the opposite is often the case for dry eye. Present clinical measurements of the tear film lipid layer are for the most part qualitative or semi-quantitative in nature. Korb, in U.S. Pat. Nos. 8,591,033 and 8,585,204, disclose a quantitative method for measuring the thickness of the tear film lipid layer. However, this method does not measure the lipid layer over the central cornea where tear film thinning and breakup due to evaporation is maximal and where it is believed a better diagnosis of dry eye can be obtained. Huth, in U.S. Pat. No. 8,602,557 B2 (incorporated herein by reference in its entirety) also disclose a quantitative method for measuring the thickness of the tear film lipid layer as part of a method to simultaneously measure the tear film aqueous layer and the corneal surface refractive index. However, this method requires as long as 475 seconds to complete the calculations for a single tear film spectrum.

SUMMARY

Thus, it is the object of the present invention to overcome the limitations of the prior art, and to increase the sensitivity, accuracy and precision of the measurement of the tear film lipid layer. Fast, accurate and precise lipid layer thickness-determination methods are also needed for the quantitative evaluation of the effects of novel dual-function lipid-supplementation tear formulas on the tear film lipid layer. Such methods are also needed to evaluate the effects of other eye drops, ophthalmic dry eye drugs and MPS solutions, and contact lenses on the tear film lipid layer.

In one embodiment, the invention provides a method for determining reflectivity of a tear film lipid layer of a patient. The method includes the steps of: measuring a tear film aqueous plus lipid layer relative reflectance spectrum using a wavelength-dependent optical interferometer; converting the measured tear film aqueous plus lipid layer relative reflectance spectrum to a calculated absolute reflectance spectrum; comparing the calculated absolute reflectance spectrum to a theoretical absolute lipid reflectance spectrum to determine a tear film lipid layer thickness; and determining a reflectivity value for the tear film lipid layer thickness at a first wavelength of light corresponding to ultraviolet, violet, or blue light.

In another embodiment the invention provides a system for determining reflectivity of a tear film lipid layer of a patient. The system includes a wavelength-dependent optical interferometer and a controller in communication with the interferometer. The controller is configured to measure a tear film aqueous plus lipid layer relative reflectance spectrum using the interferometer, convert the measured tear film aqueous plus lipid layer relative reflectance spectrum to a calculated absolute reflectance spectrum, compare the calculated absolute reflectance spectrum to a theoretical absolute lipid reflectance spectrum to determine a tear film lipid layer thickness, and determine a reflectivity value for the tear film lipid layer thickness at a first wavelength of light corresponding to ultraviolet or blue light.

In yet another embodiment the invention provides a method for selecting an intraocular lens for a patient. The method includes the steps of: determining a tear film lipid layer thickness for the patient; determining a reflectivity value for the tear film lipid layer thickness at a first wavelength of light corresponding to ultraviolet, violet, or blue light; and identifying an intraocular lens for attenuating or blocking at least one wavelength of light corresponding to ultraviolet, violet, or blue light.

In still another embodiment, the invention provides a method of determining tear film lipid layer thickness. The method includes the steps of: measuring a tear film aqueous plus lipid layer relative reflectance spectrum using a wavelength-dependent optical interferometer; converting the measured tear film aqueous plus lipid layer relative reflectance spectrum to a calculated absolute reflectance spectrum; iteratively comparing the calculated absolute reflectance spectrum to a plurality of theoretical absolute reflectance lipid spectra to generate a plurality of tear film lipid layer thickness estimates; determining a standard error for the plurality of tear film lipid layer thickness estimates; and identifying a correct lipid layer thickness based on the standard error.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Human tear film lipid layer thickness is believed to be between 20-200 nm. Central corneal tear film lipid layer thickness rarely exceeds about 120 nm, however, and also can be less than 20 nm in thickness. Normal wavelength-dependent optical interferometric methods for the determination of thin film thickness, based upon the analysis of the increasing number of cosine-function spectral oscillations with thickness, are unsuitable for this range. This is so because even at 200 nm thickness, only half an oscillation is visible within the 575-1075 nm spectral wavelength range of the typical optical interferometer (FIG. 1).

Figure 1:
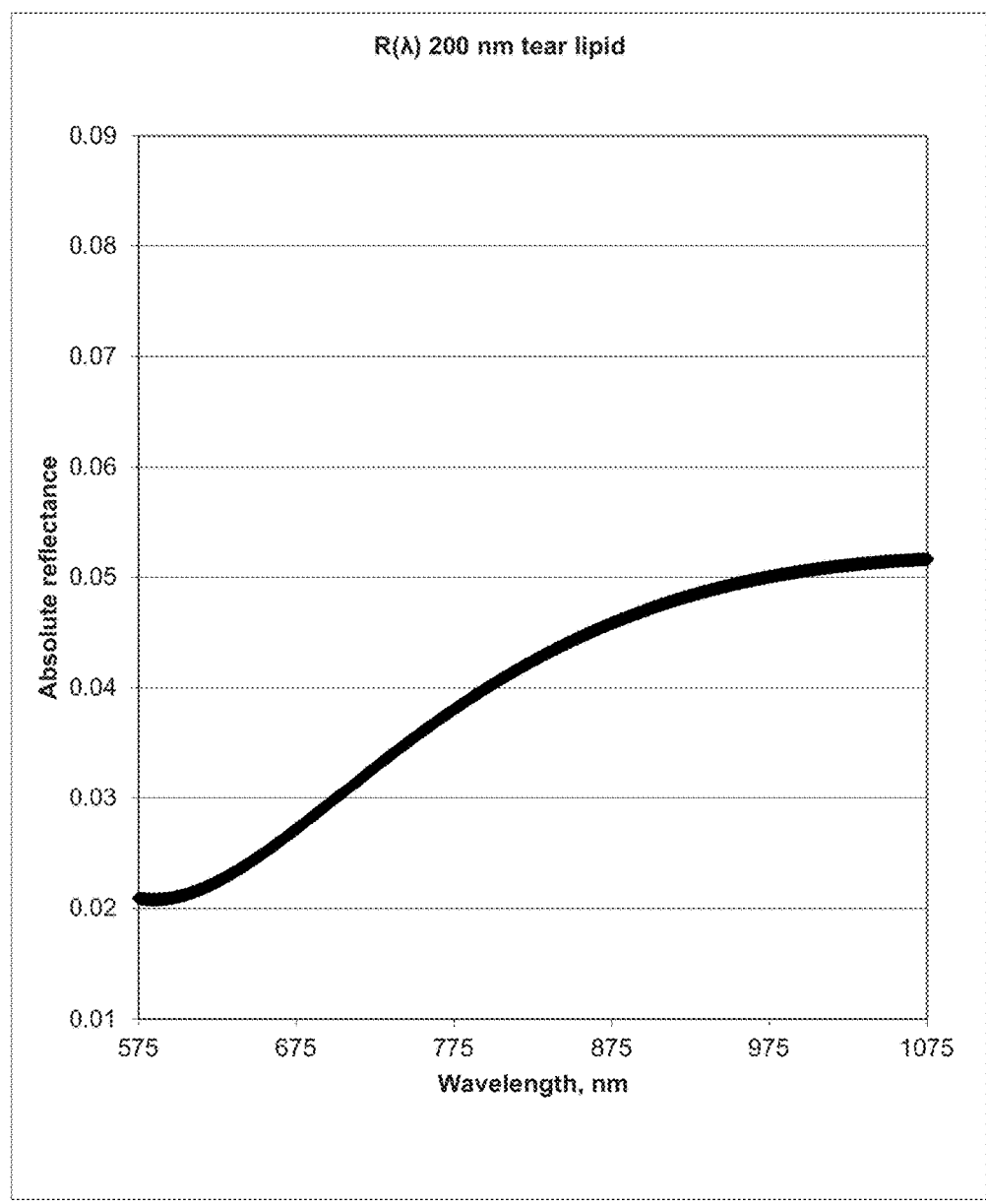
FIG. 1 shows absolute reflectance for a 200 nm tear lipid film layer measured in a wavelength range of 575 nm to 1075 nm.

Accordingly, the answer to this problem is to base the thicknesses upon absolute optical reflectivity, also illustrated in FIG. 1, where absolute reflectivity of a 200 nm lipid layer is 0.02=2% at 575 nm. Thus, one needs to compare the absolute reflectivity spectrum of a tear lipid layer to a standard reflectivity spectrum such as seen in FIG. 1. The approach to achieving this is disclosed herein.

Interferometry measurements are typically determined as relative percent light reflection values, where the measurements from a subject's tear film and cornea are expressed relative to measurements obtained from a reference material (e.g. a particular glass material having a radius of curvature comparable to that of a cornea, e.g. ranging from 7-9 mm, in particular 7.75 mm). The ratio of the light reflectance from the subject's tear film and cornea, R(λ) sample, to the light reflectance from the reference, R(λ) reference, is multiplied by 100 by typical spectrometer and CCD detector software, so that the final relative light reflection values are expressed as percentages; the percentage values are determined for a range of wavelengths to obtain a spectrum. Thus, the y-axis of a measured spectrum corresponds to 100×R(λ) sample/R(λ) reference.

As an initial step in the development of the methods of the present invention, the theoretical absolute spectra for lipid layers of various thicknesses were calculated. Given that these theoretical absolute spectra have similar shapes or slopes to one another, but different absolute optical reflectivity at different wavelengths, correlating the theoretical absolute spectra with observed spectra requires determining the absolute reflectance spectrum from the measured data and correlating the absolute spectra with the theoretical spectra. Experimentation is required, however, to account for discrepancies between theoretical predicted spectra and actual measured spectra. Lipid layer standards of known thicknesses are not available and so it is not possible to perform calibrations using lipids. Instead, a series of calibrations was performed using commercially-available standards having layers of silicon dioxide of known thicknesses, comparable to thicknesses of tear film lipid layers. The measured spectra for the silicon dioxide standards were compared to the predicted theoretical absolute spectra for silicon dioxide layers of the same thicknesses and a correction algorithm was produced which can be used to obtain the absolute reflectance values for measured tear film lipid layers. The correction algorithm accounts for changes in light reflection arising from the geometry of a curved reference lens or from non-orthogonal placement of a flat reference surface with respect to incident light and from out-of-focus light reflection.

In various embodiments, the disclosed methods are modifications of a procedure for calculation of absolute reflectance of the presumed tear structure, involving an air interface with a single lipid layer overlying an aqueous layer.

In the aforementioned procedure, $n_0$, $n_1$, and $n_2$ are the refractive indices of the air, lipid layer, and aqueous layer, respectively, for which fixed values of $n_0=1$, $n_1=1.48$, and $n_2=1.33$ have been used. In one embodiment of the present invention, the respective complex refractive indices are used for $n_1$ and $n_2$, each of which changes with wavelength.

The Fresnel indices of reflection $r_1$ and $r_2$ for the air-lipid and lipid-aqueous interfaces are, respectively:

$$r_1=(n_0-n_1)/(n_0+n_1) \text{ and } r_2=(n_1-n_2)/(n_1+n_2)$$

Since energy is proportional to the square of amplitude, $R(\lambda)=R \times R^*=|R^2|$, where $R^*$ is the conjugate complex numbers of R. Thus, from Euler's equation:

$$R(\lambda)=(r_1^2+r_2^2+2r_1r_2 \cos 2\delta_2)/(1+r_1^2r_2^2+2r_1r_2 \cos 2\delta_1=1-(8n_0n_1^2n_2)/((n_0^2+n_1^2)(n_1^2+n_2^2)+ 4n_0n_1^2n_2+(n_0^2-n_1^2)(n_1^2-n_2^2)\cos 2\delta_1)$$

where a phase difference between two waves $r_1$ and $r_2$, is $2\delta_1$ and $$2\delta_1 = (4\pi/\lambda)n_1 d \cos \phi_1$$

where $\phi_1$ is the angle of refraction of the incident light upon the lipid layer,
which=9.369° for the wavelength-dependent optical interferometer used in the methods of the present invention, thus $\cos \phi_1$=0.986659.

The complex refractive indices for $n_1$ (lipid) and $n_2$ (aqueous) are used:

$$n_1 = nd = y = \text{sqrt}(1 + (((-851.03)*x*x)/(x*x-(816.139))) +$$
$$(((420.267)*x*x)/(x*x-(-706.86)))$$

plus $(((431.856)*x*x)/(x*x-(2355.29))))$ where x=wavelength
and where nd=Sellmeier equation form of tear meibomian lipid refractive index derived from primary refractive index data from Tiffany, J M. Refractive index of meibomian and other lipids. *Current Eye Research*. 5(11), 1986; 887-889: 430 nm:nd=1.5126; 450 nm:1.5044; 510 nm: 1.4894; 590 nm:1.4769; 710 nm:1.4658. The Sellmeier equation coefficients were derived by fitting the limited Tiffany data (no data exist beyond 710 nm, where most of the spectral range of the interferometer exists (spectral range: 559-1085 nm)) first to a polynomial (nd=5.04e-7 x2−0.00736x+1.73481, wherein x=wavelength) to generate forecasted refractive index values at 600, 620, 640 and 680 nm, followed by fitting the Tiffany+forecasted refractive index data set to the Sellmeier equation format wherein refractive index data beyond 710 nm could be calculated and utilized. The Sellmeier equation format for lipid refractive index data is believed to provide more accurate refractive index information, which is critical for accurate lipid layer thickness calculations.

$$n_2 = 1.32806 + 0.00306*(1000/\lambda)^2$$

Figure 2:
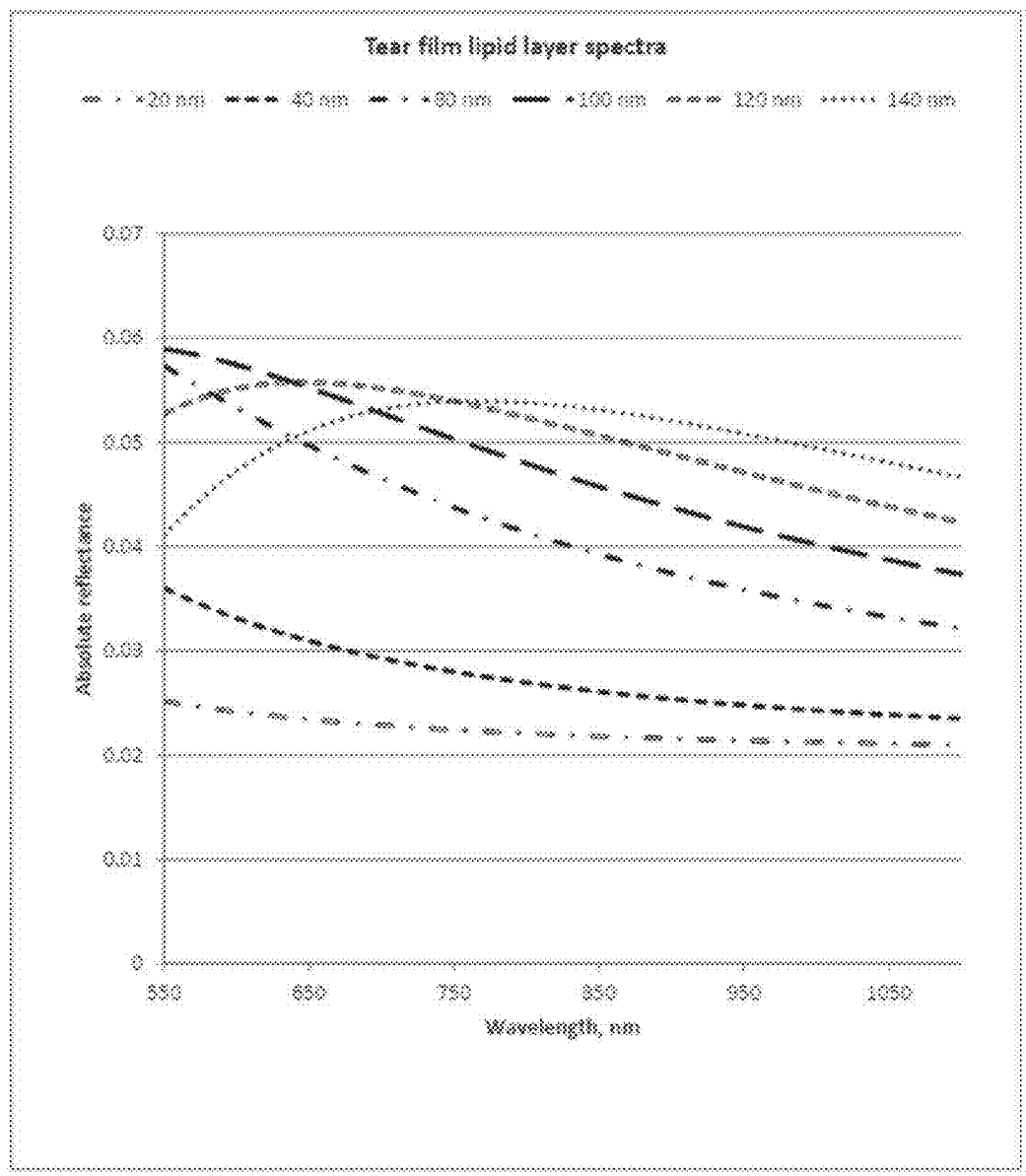
FIG. 2 shows calculated absolute reflectance spectra for lipid layers thicknesses in a range of 0-140 nm.

Using the above equations, an Excel spreadsheet is created in which the values of the three refractive indices $n_0$, $n_1$ and $n_2$ are calculated (except for $n_0$, which is always 1) for the wavelengths within the wavelength range measured by the interferometer (e.g., for wavelengths between 559-1085 nm). Then, using the expanded Euler's equation with all terms, $R(\lambda)$ is calculated for a series of lipid layer thicknesses, d. The results from 575-1075 nm are seen in FIG. 2, presenting a series of absolute-value reflectance spectra for lipid layers of various thicknesses.

The spectrum (not shown) for a lipid layer of 0 nm thickness is very flat, lies just below that of a 20 nm thick lipid layer and produces an absolute reflectance of 0.02% of the incident light at 550 nm. It can be seen in FIG. 2 that there is little difference in the slopes of the lipid layer spectra between 20-100 nm thicknesses, further reinforcing the need to base lipid layer thickness calculations upon absolute reflectance values rather than parameters such as the slope or shape of the spectra. Thus, a 20 nm lipid layer will reflect about 0.025=2.5% of the incident light at 550 nm, whereas a 100 nm lipid layer will reflect about 0.06=6% of the incident light at 550 nm. At 120 nm thickness and larger, the slope of absolute reflectance begins to change from a negative slope to a flat slope. Beyond 140 nm thickness, as seen in FIG. 1 for a 200 nm thickness, the slope becomes positive. Slope evaluation at 120 nm and beyond becomes a valuable tool to distinguish between a thin or thick lipid layer.

Figure 3:
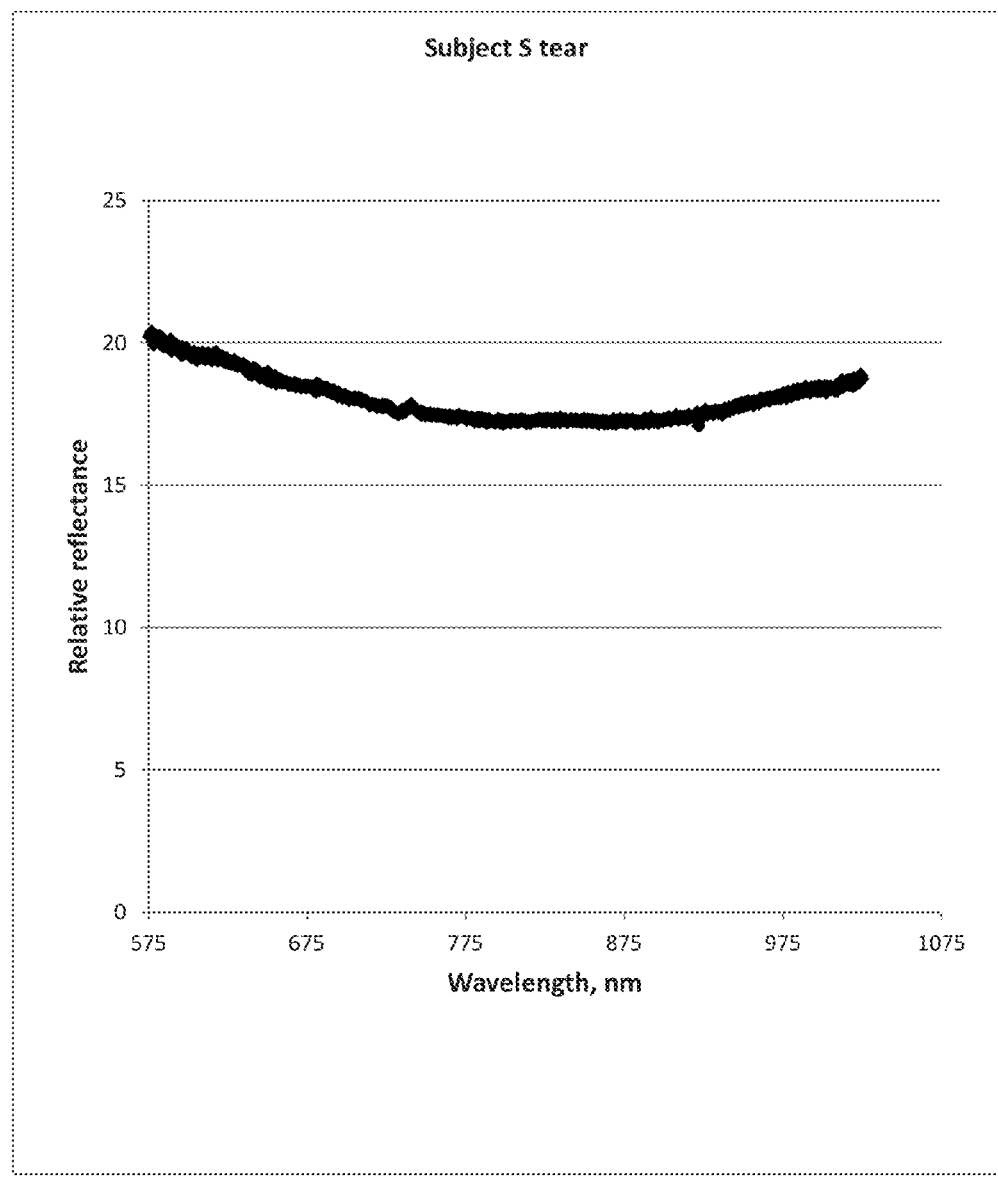
FIG. 3 shows an unmodified tear film lipid spectrum obtained using an interferometer.

Thus, for the majority of tear film lipid layers between 0-100 nm thickness, it is not a simple exercise to measure a tear lipid spectrum with a wavelength-dependent optical interferometer and compare it to one of the above absolute reflectance spectra. This is illustrated in FIG. 3, which shows an unmodified measured tear lipid spectrum.

Accordingly, each measured spectrum must be converted to a calculated absolute spectrum and then compared to the absolute reflectivity derived from theory. This comparison must be accomplished mathematically.

This new procedure required development and validation with thin film standards. Since thin lipid film standards are not available, thin $SiO_2$ film standards, produced via vapor deposition of $SiO_2$ onto pure flat Silicon wafer substrates were used. These standards are commercially available (VLSI Standards, Inc. San Jose, Calif. 95134-2006) and calibrated to within 0.1-0.01 nm thickness by NIST. The following $SiO_2$ standards were employed (the 0 nm standard was a pure silicon wafer without $SiO_2$; Table 1).

TABLE 1

| $SiO_2$ Actual thickness, nm |
|---|
| 0 |
| 48.26 |
| 95.01 |
| 188.58 |

Absolute reflectivity of these $SiO_2$ films were calculated, using the same procedure with the expanded Euler equation above, substituting the complex refractive indices below for $n_1$ and $n_2$ ($n_0$=air=1, as before).

$$SiO_2\ n_1 = -9.3683E\text{-}11x^3 + 2.5230E\text{-}07x^2 - 2.3810E\text{-}04x + 1.5302E+00$$

$$Si\ n_2 = \text{SQRT}(1 + ((5.66474*\lambda*\lambda)/((\lambda*\lambda)-119153)) + ((5.29869*\lambda*\lambda)/(\lambda*\lambda-(51556.1))) + ((-24642*\lambda*\lambda)/((\lambda*\lambda)-(-146300000000)))))$$ (conversion of raw $n_2$ data to the Sellmeier equation form)

Figure 4:
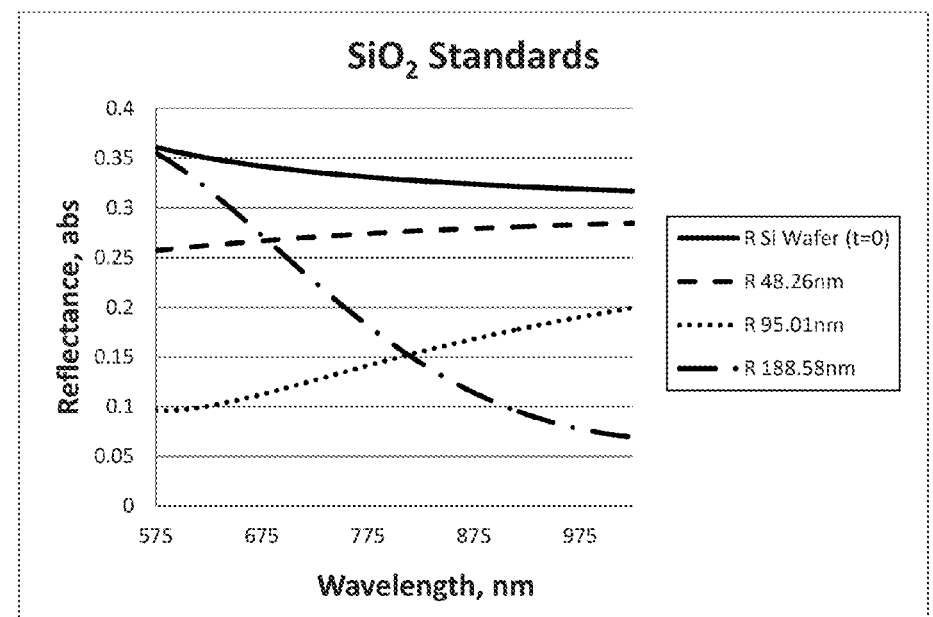
FIG. 4 shows absolute reflectance spectra for $SiO_2$ layers having thicknesses from 0-188.6 nm.

The latter equation for the refractive index of pure silicon is in the form of the Sellmeier equation. This equation form is considered to provide very accurate values of the refractive index as a function of wavelength. Not all refractive index data are provided in this form, however. The resulting absolute reflectance spectra are seen in FIG. 4.

Interferometer-measured spectra for $SiO_2$ standards, as for measured tear film lipid spectra, are expressed as relative % reflectance, since the measured reflectance from a thin film is measured relative to the measured reflectance from a reference. The y-axis of a measured spectrum corresponds to 100×$R(\lambda)$ meas. sample/$R(\lambda)$ meas. reference.

A number of different references can be used, although the best reference for tear film spectra is one with the same radius of curvature as the cornea (r=7.75 mm), to allow for the same reflectance geometry. In certain embodiments, a spherically-curved BK7 glass reference lens is used for this purpose. A pure flat silicon wafer can also be used as the reference for the $SiO_2$ standards, since both surfaces are flat. The conversion procedure to convert a measured $SiO_2$ or tear film spectrum to a calculated absolute reflectance spectrum is to first divide by 100 and then to multiply the ($R(\lambda)$ meas. Sample/$R(\lambda)$ meas. Reference)×$R(\lambda)$ absolute reference. Here, $R(\lambda)$ absolute reference is the calculated theoretical reflectivity of the reference and the abbreviation for absolute when used throughout this disclosure will be: abs. This result can then be compared mathematically to a theoretical SiO2 or tear lipid spectrum, as illustrated in FIG. 4 for $SiO_2$. In order to accomplish this procedure, one has to first calculate R(λ) absolute reference (for pure Silicon or BK7). The equation which is used is derived from the following equations.

If incident light is unpolarized, and since $R=|r|^2$ (since reflected intensity is proportional to the square of the modulus of the electric field amplitude and the dielectric function), then total $R=(r_s^2+r_p^2)/2$.

Also, from Snell's law, where $\sin \psi=(n_1/n_2) \sin \phi$, $\cos \psi=(1-(n_1^2/n_2^2)\sin^2\phi)^{1/2}$.

Then, from the theory of interface reflection between two isotropic materials (e.g. air and an isotropic solid such as Si or BK7), the indices of reflection are determined as follows:

$$r_s=(n_1 \cos \phi - n_2 \cos \psi)/(n_1 \cos \phi + n_2 \cos \psi)=(n_1 \cos \phi - n_2(1-(n_1^2/n_2^2)\sin^2\phi)^{1/2})/(n_1 \cos \phi + n_2(1-(n_1^2/n_2^2)\sin^2\phi)^{1/2}), \text{ and}$$

$$r_p=(n_2 \cos \phi - n_1 \cos \psi)/(n_2 \cos \phi + n_1 \cos \psi)=(n_2 \cos \phi - n_1(1-(n_1^2/n_2^2)\sin^2\phi)^{1/2})/(n_2 \cos \phi + n_1(1-(n_1^2/n_2^2)\sin^2\phi)^{1/2})$$

These equations may also be written as:

$$r_s=(n_1 \cos \phi - (n_2^2 - n_1^2 \sin^2\phi)^{1/2})/(n_1 \cos \phi + (n_2^2 - n_1^2 \sin^2\phi)^{1/2}),$$

since $(n_2^2 - n_1^2 \sin^2\phi)^{1/2} n_2((n_2^2/n_2^2)-(n_1^2/n_2^2)\sin^2\phi)^{1/2} = n_2(1-(n_1^2/n_2^2)\sin^2\phi)^{1/2}$ and $$r_p=(n_2 \cos \phi - n_1(1-(n_1^2/n_2^2)\sin^2\phi)^{1/2})/(n_2 \cos \phi + n_1(1-(n_1^2/n_2^2)\sin^2\phi)^{1/2})$$

Then, since $n_1=\text{air}=1$, the equations above can be combined using the relationship $R \text{ abs}=(r_s^2+r_p^2)/2=R(\lambda)$ abs Si or $R(\lambda)$ abs BK7 (i.e. to obtain calculated absolute reflectance values for silicon or BK7 glass):

$$R(\lambda)\text{abs Si}=(40.986659-D3*SQRT(1-(0.162799/D3)^2))/(0.986659+D3*SQRT(1-(0.162799/D3)^2)))^2+(((SQRT(1-(0.162799/D3)^2))-D3*0.986659)/((SQRT(1-(0.162799/D3)^2))+D3*0.986659))^2)/2$$

where D3=Sellmeier refractive index for Si at each λ, and where $0.986659=\cos \phi$ and $0.162799=\sin \phi$ and where each wavelength is an exact wavelength measured by the interferometer.

R(λ) abs BK7 is calculated for each wavelength using the same equation, except D3=Sellmeier refractive index for BK7 at each λ.

Sellmeier BK7 $n=SQRT(1+(1.03961212*G3*G3)/(G3*G3-0.00600069867)+(0.231792344*G3*G3)/(G3*G3-0.0200179144)+(1.01046945*G3*G3)/(G3*G3-103.560653))$ where G3=interferometer wavelength in microns (BK7 refractive index ref=Schott technical information document TIE-29 (2005)).

Figure 5:
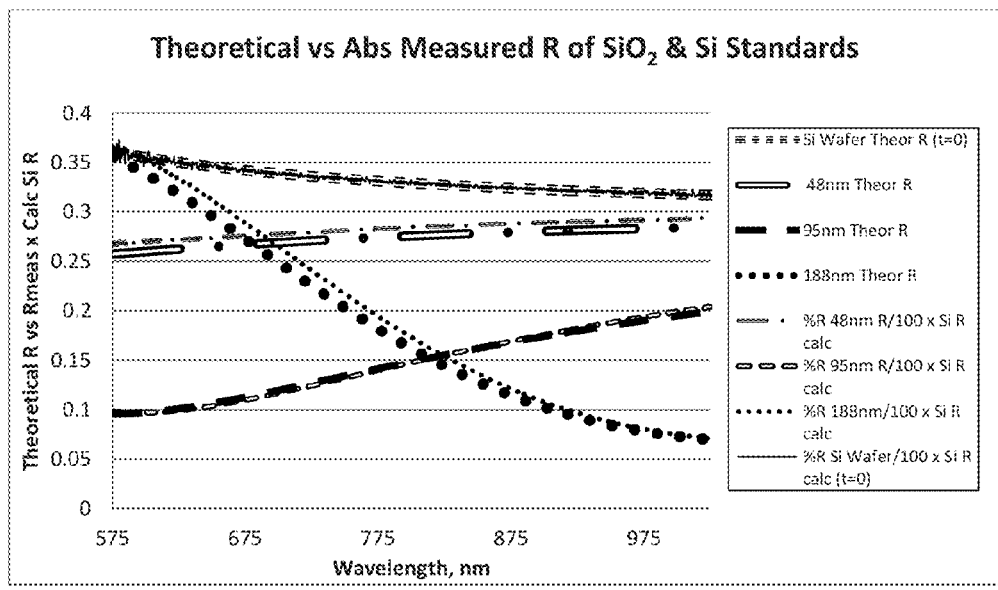
FIG. 5 shows the results of converting measured relative $SiO_2$ spectra to calculated absolute reflectance spectra, where each absolute reflectance spectrum obtained from measured data is compared to an equivalent calculated theoretical spectrum.

FIG. 5 shows the results of converting measured SiO$_2$ spectra (using a 4V or 4.5V light source voltage, 20 msec single scan) to calculated absolute reflectance spectra for various silicon reference standards. The measured relative spectra are first divided by 100 and then multiplied times R(λ) abs Si reference (Si abs R calculated) to obtain R(λ) abs SiO$_2$ sample spectra.

It can be seen that there are some relatively small differences between the theoretical and calculated absolute spectra. These differences can be mathematically calculated using an algorithm which compares the calculated absolute spectra to theoretical absolute spectra of various SiO$_2$ films of varying thicknesses. In one particular embodiment, this is accomplished by creating a Statistica software program (StatSoft®, Tulsa, Okla.) based upon the expanded Euler equation from above:

$$V5=(1-((8*v1*v2**2*v3)/((v12+v22)*(v22+v32))+4*v1*v2**2*v3+((v12-v22)*(v22-v32)*(\cos(4*3.14159*v2*a*0.98666/v4))))$$

where v5=R(λ) SiO$_2$ measured sample×R(λ) abs Si reference (Si abs R calculated)/100 and where v1=$n_0$ air=1, v2=$n_1(\lambda)$ SiO$_2$, v3=$n_2(\lambda)$ Si, v4=measured λ, and the variable a, the fitted film thickness.

As shown below, the wavelength range for SiO$_2$ thin film standards must be limited to 575-1025 nm, to avoid signal weakness/potential optical aberration at the wavelength extremes. Thus, the program requires the input of five columns of calculated and measured data input as variables (i.e. v1-v5). The Non-linear Estimation method within the Statistica software is used, wherein the equation for v5 above is input as the function to be estimated into the space provided in the user specified regression, least squares module. The Statistica software program uses the Levenburg-Marquardt algorithm to achieve a minimum in the sum of squares of the differences between theoretical R and the product of R(λ) SiO$_2$ measured sample×R(λ) abs Si reference (Si abs R calculated)/100 at each wavelength. In various embodiments, other mathematical algorithms for fitting data are available within Statistica and other software platforms and can also be employed. This software module requires the number of calculation/fitting iterations to be selected. In one embodiment, fifty iterations were found to be acceptable, although other lower or higher numbers of iterations are also acceptable and can be readily determined by an evaluation of the p-level of the fit. All p-levels for thin films were found to be 0.00 and are thus highly significant.

The program also requires a starting value for the variable a-term, the fitted film thickness. This is indicated in the column labeled "STAT Input" in Table 2 below for the SiO$_2$ thin film standards. It was discovered through experiments with tear film spectra, presented below, that a starting value for the a-term that is too far from the actual thin film thickness value may converge to an incorrect result. It is believed that this may be a result of convergence to a local minimum in the least squares sum. Considerable time may be required to run the program multiple times with different starting values until the correct value is found. Moreover, the correct tear film lipid layer thickness is not known prior to calculation and thus the correct starting value is not known. Thus, selecting the proper starting value is important not only for a fast method, but also to achieve correct results. The human tear film lipid layer thickness typically ranges between 0 and 120 nm in thickness. Thus, in one particular embodiment a starting value of 65 nm has been determined to produce correct results for tear film lipid layer thickness between 0 and about 100 nm thickness as well as for SiO$_2$ thin film standards between 0 and 95 nm. Other starting values may be employed where necessary in cases where a 65 nm starting value is incorrect, as is the case for the 188.58 nm SiO$_2$ thin film standard, in which case a 200 nm starting value was used.

Subsequently, the validity of the method was demonstrated using a curved BK7 glass reference lens having an identical radius of curvature as the human cornea, 7.75 mm.

This particular lens is used as a reference when making measurements of the human tear film in order to achieve optics as close as possible to those during the human tear film measurements.

Figure 6:
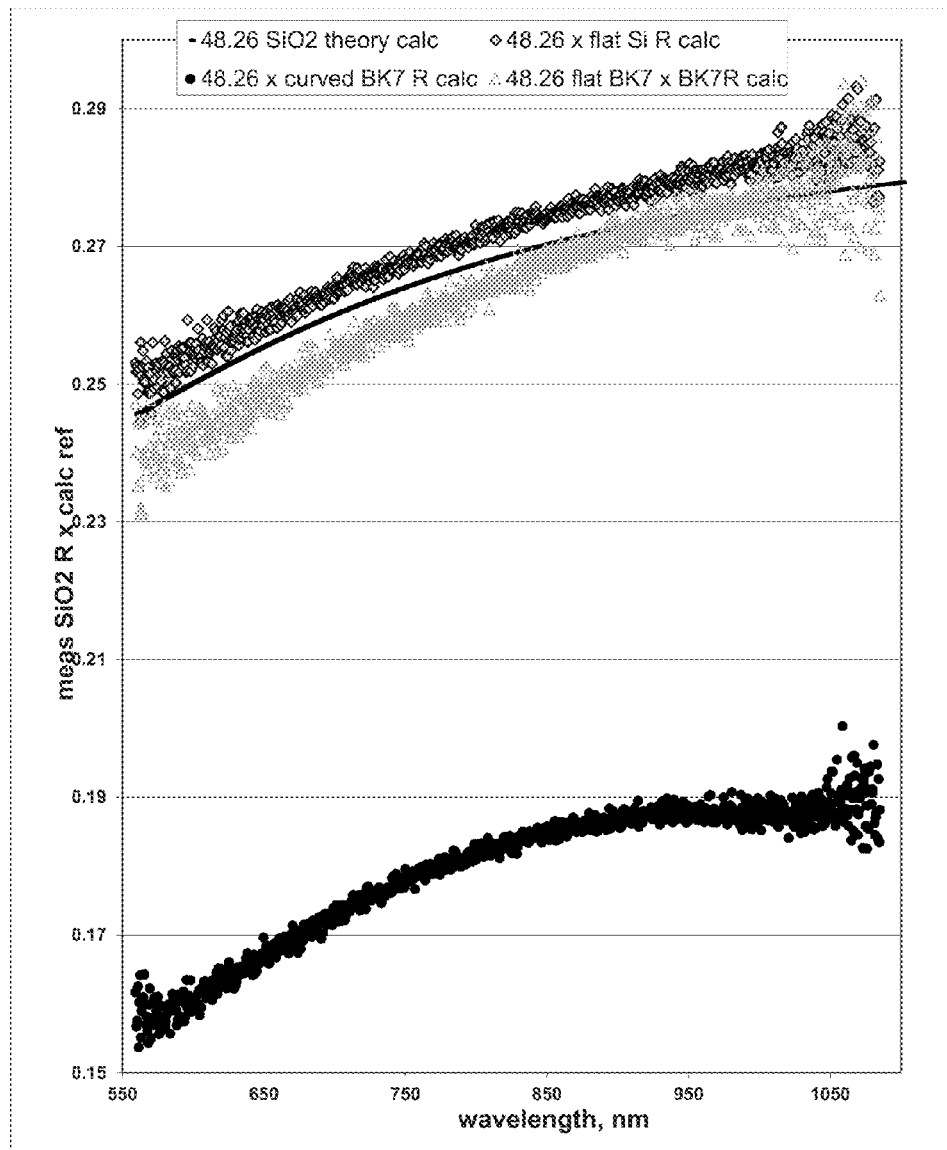
FIG. 6 shows the comparison between a calculated theoretical spectrum for a 48.26 nm SiO2 thin film standard compared to calculated absolute reflectance spectra obtained by converting measurements of the relative reflectance spectra for the 48.26 nm $SiO_2$ thin film standard which were measured relative to various reference materials, including a flat silicon wafer, a flat BK7 glass plate, and a curved BK7 glass lens having an identical radius of curvature as the human cornea, i.e. 7.75 mm.

A similar mathematical process was completed using measured SiO$_2$ thin film standard spectra with different reference materials. FIG. 6 shows absolute reflectance spectra obtained by converting measurements of the relative reflectance spectra for the 48.26 nm SiO$_2$ thin film standard which were measured relative to various reference materials, including a flat silicon wafer, a flat BK7 glass plate, and a curved BK7 glass lens having an identical radius of curvature as the human cornea, i.e. 7.75 mm. The absolute spectra, determined from measured relative spectra, are graphed relative to the calculated absolute spectrum for a 48.26 nm SiO$_2$ thin film. FIG. 6 shows that when either a flat Silicon wafer or flat BK7 reference lens is used instead of the curved BK7 lens, the spectra determined from the measured relative reflectance spectra closely match the respective theoretical spectrum. However, when the curved BK7 glass lens was used as the reference, the absolute reflectance spectrum that was obtained does not overlay the theoretical spectrum and instead is shifted downward. Without being limited as to theory, this is likely because the geometry of light reflection from the flat 48.26 nm SiO$_2$ and the flat BK7 standards is not the same as the light reflection from the curved BK7 glass lens.

Similar results were obtained with the other SiO$_2$ thin film standards (not shown). What became evident is that a final multiplier term (b) is required. The measured spectra must be multiplied by the b-term to match the theoretical spectra. Moreover, the b-term is a variable which changes between measured spectra. The b-term is in essence a light focusing term and corrects for non-identical focusing between the reference lens measurement and the human tear film measurement. Thus, the expanded Euler equation becomes:

$$V5=(1-((8*v1*v2**2*v3)/((v12+v22)*(v22+v32)+4*v1*v2**2*v3+((v12-v22)*(v22-v32)*(\cos(4*3.14159*v2*a*0.98666/v4))))))*b$$

where v5=R($\lambda$) SiO$_2$ measured sample×R($\lambda$) abs Si reference (Si abs R calculated)/100 and where v1=n$_0$ air=1, v2=n$_1$($\lambda$) SiO$_2$, v3=n$_2$($\lambda$) Si, v4=measured $\lambda$, and the variable a, the fitted film thickness, and the variable b, the final correction term which moves the measured spectrum up or down on the theoretical R axis (y-axis) to achieve a match with theory.

In one embodiment, the software program requires the b-term to be on the right-hand side of the equation and at the end of the equation, since it requires starting input values for any variables (here a and b) to be in the same order (left to right) in which they appear in the equation program line and the variable input value program line. Since the right side of the above equation is the calculated theoretical reflectance which iteratively matches the calculated measured absolute reflectance on the left hand side, the b-term may have a value less than 1 (a b-term on the right side of 0.5 would be equivalent to a b-term on the left side of 2.0). It was determined through experiments varying the starting value of the b-term from 0 to 1.30 that the b-term value can start at a relatively wide range of values, for example between 0.40-0.80 or between 0 and 1.30, so that the program achieves the correct thickness. The center of the b-term range is about 0.66 and thus this is a good starting value.

All scan times herein for the SiO$_2$ thin film standards are single 20 msec scans, whereas tear film spectra are typically sums of twelve 21 msec scans. The program is very fast, calculating results for a single spectrum in under a second and results for 50 spectra in 11 seconds. The results for the SiO$_2$ thin film standards are shown in Table 2 below.

TABLE 2

| Actual SiO2 Thickness, nm | STAT Input | | Meas. SiO2 Thickness, nm | Avg. Meas. SiO2 Thickness, nm | B |
|---|---|---|---|---|---|
| 0 | 65 | a | 4.42 | | |
|  | 0.66 | b | | | 1.002 |
| 48.26 | 65 | a | 47.57 | 48.12 | |
|  | 0.66 | b | | | 1.026 |
| 48.26 | 65 | a | 48.37 | | |
|  | 0.66 | b | | | 0.994 |
| 48.26 | 65 | a | 48.43 | | |
|  | 0.66 | b | | | 1.035 |
| 95.01 | 65 | a | 98.54 | 98.56 | |
|  | 0.66 | b | | | 1.062 |
| 95.01 | 65 | a | 98.57 | | |
|  | 0.66 | b | | | 1.062 |
| 95.01 | 65 | a | 98.55 | | |
|  | 0.66 | b | | | 1.063 |
| 188.58 | 200 | a | 190.53 | 190.55 | |
|  | 0.66 | b | | | 1.033 |
| 188.58 | 200 | a | 190.55 | | |
|  | 0.66 | b | | | 1.032 |
| 188.58 | 200 | a | 190.56 | | |
|  | 0.66 | b | | | 1.030 |

Figure 7:
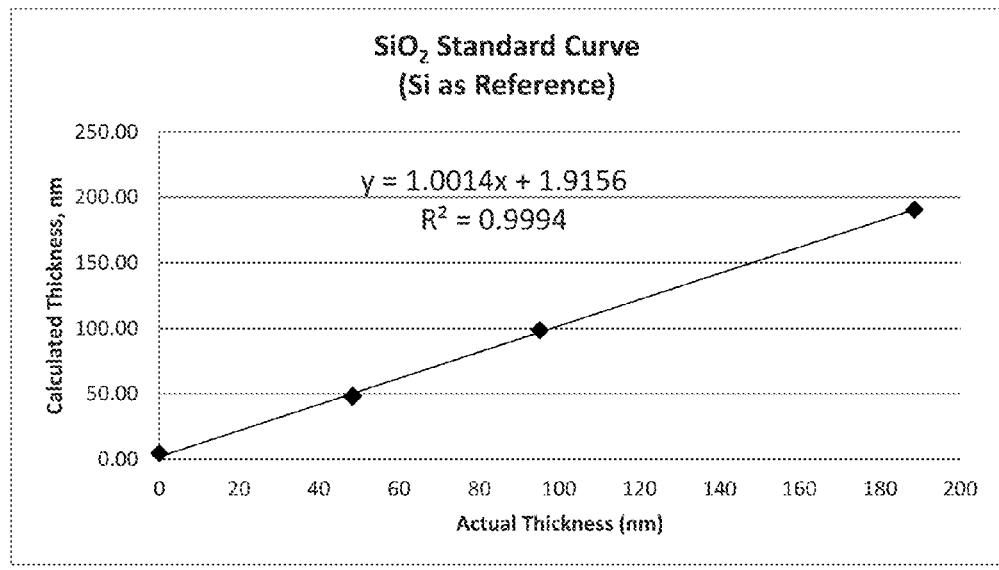
FIG. 7 shows a standard curve comparing the actual thickness (in nm) of the SiO2 thin film standards to the thickness determined using the methods disclosed herein.

FIG. 7 shows a standard curve comparing the actual thickness (in nm) of the SiO$_2$ standards to the thickness determined using the methods disclosed herein. As can be seen, the values obtained using the disclosed methods closely match the actual thicknesses of the silicon dioxide standards. These are excellent results, with only a 1.8 nm error on average, maximum error of 3.6 nm and standard curve and slope=1.0014 and 1.9156 nm, respectively, demonstrating that the basic mathematics of the disclosed methods are correct. The observed absolute error results are expected to decrease with higher scan-number values for each standard and longer scan times.

Table 3 shows the results of experiments with tear film interferometry spectra and demonstrates that using a starting value for the tear film lipid layer thickness (i.e. the a-term) which is too far from the actual lipid thickness value can produce incorrect results. Lipid thickness values for these spectra were verified with the '557 method. Starting values for the b-term in all cases were 0.66. Spectrum subj18rt11 is that of a tear film during Oasys contact lens wear, indicating that the method of the present invention is suitable for measuring tear film lipid layers during contact lens wear.

TABLE 3

| Spectrum | Statistica lipid thickness result, nm | Statistica b-term result | Stat lipid starting thickness (a-term, nm) |
|---|---|---|---|
| sub7base#49 | 82.17 | 0.2738 | 50, 90, 100 ok |
| sub1#118 | 25.26 | 0.9987 | 65, 75 ok; 100 no: 130.79 w b = .4416 |
| sub2AY | 51.99 | 0.9949 | 40, 50, 65, 75 ok; 100 no: 102.95 w b = .6396 |
| sub21#43 | 31.78 | 0.3701 | 40, 50, 65, 70 ok; 75 no: 110.86 w b = 1828 |

TABLE 3-continued

| Spectrum | Statistica lipid thickness result, nm | Statistica b-term result | Stat lipid starting thickness (a-term, nm) |
|---|---|---|---|
| sub2CV | 78.18 | 0.9974 | 50, 65, 75, 100 ok |
| subj18rt11 | 7.94 | 0.9322 | 65 ok; 73, 100 no: 132.28 w b = .3757 |

Figure 8:
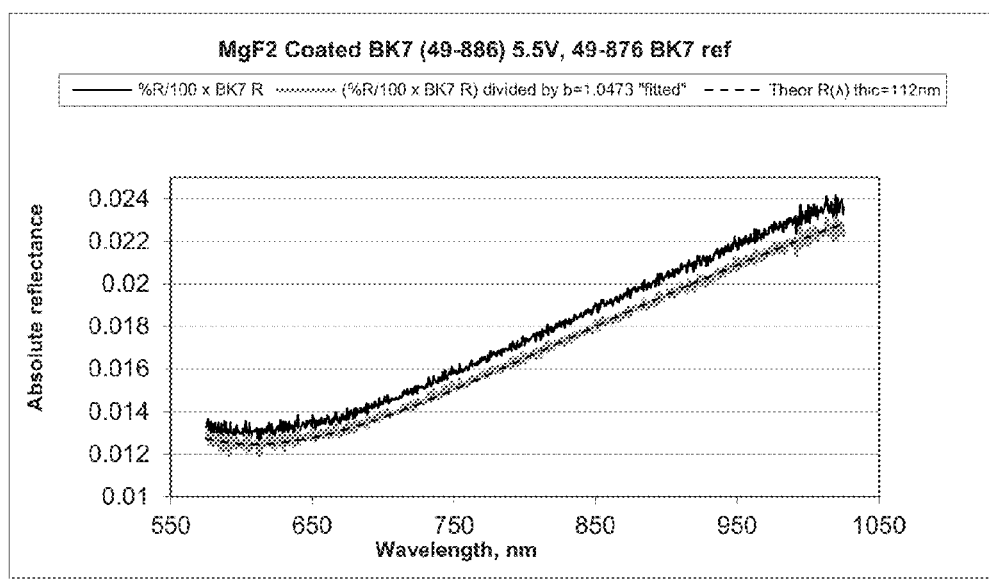
FIG. 8 shows a theoretical spectrum (dashed line, - - - ) vs. b-term fitted spectrum (light grey line, overlapping dashed line) and spectrum without the b-term fit (black line).

FIG. 8 shows the results of using the methods disclosed herein to measure a thin $MgF_2$ film on a curved BK7 lens surface. This sample serves as a surrogate for a human tear lipid film on the curved aqueous corneal surface. The results show the $MgF_2$ film to be 111.98 nm thick. Here, the b-term started at 1 and converged to a value of 1.0473. The measured and theoretical spectra overlay one another exactly, further confirming the method herein. FIG. 8 shows a theoretical spectrum (dashed line, - - - ) vs. b-term fitted spectrum (light grey line, overlapping dashed line) and spectrum without the b-term fit (black line). Materials: $MgF_2$-coated BK7 lens, Edmund Optics (Barrington N.J. 08007) part 49-886, radius of curvature=7.75 mm, used with uncoated BK7 ref lens, Edmund Optics part 49-876, radius of curvature=7.75 mm.

Figure 9:
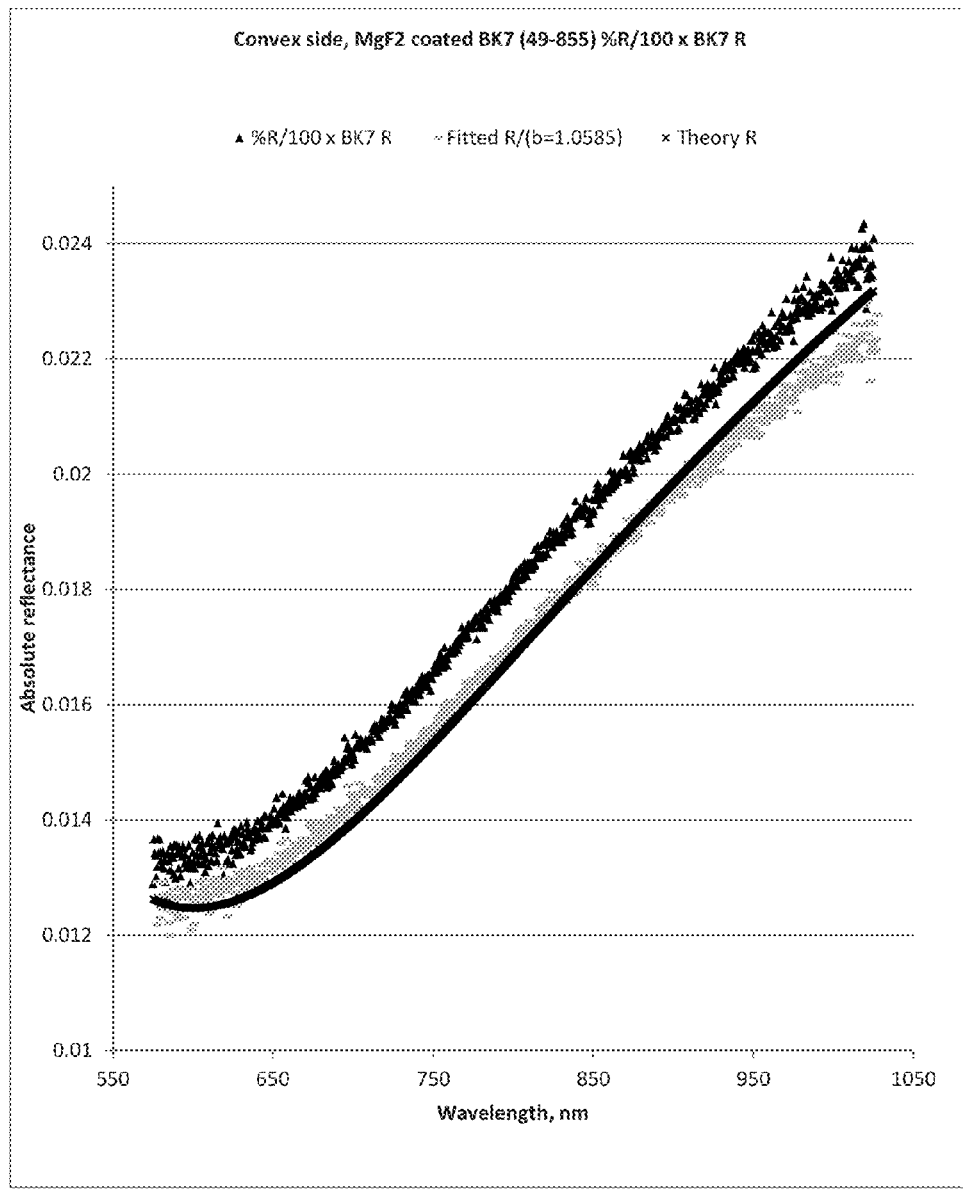
FIGS. 9 and 10 show calculated absolute reflectance spectra for the MgF$_2$ coating on the convex (FIG. 9) and the flat (FIG. 10) faces of a coated BK7 lens, both compared to a calculated theoretical spectrum for the MgF$_2$ coating.
Figure 10:
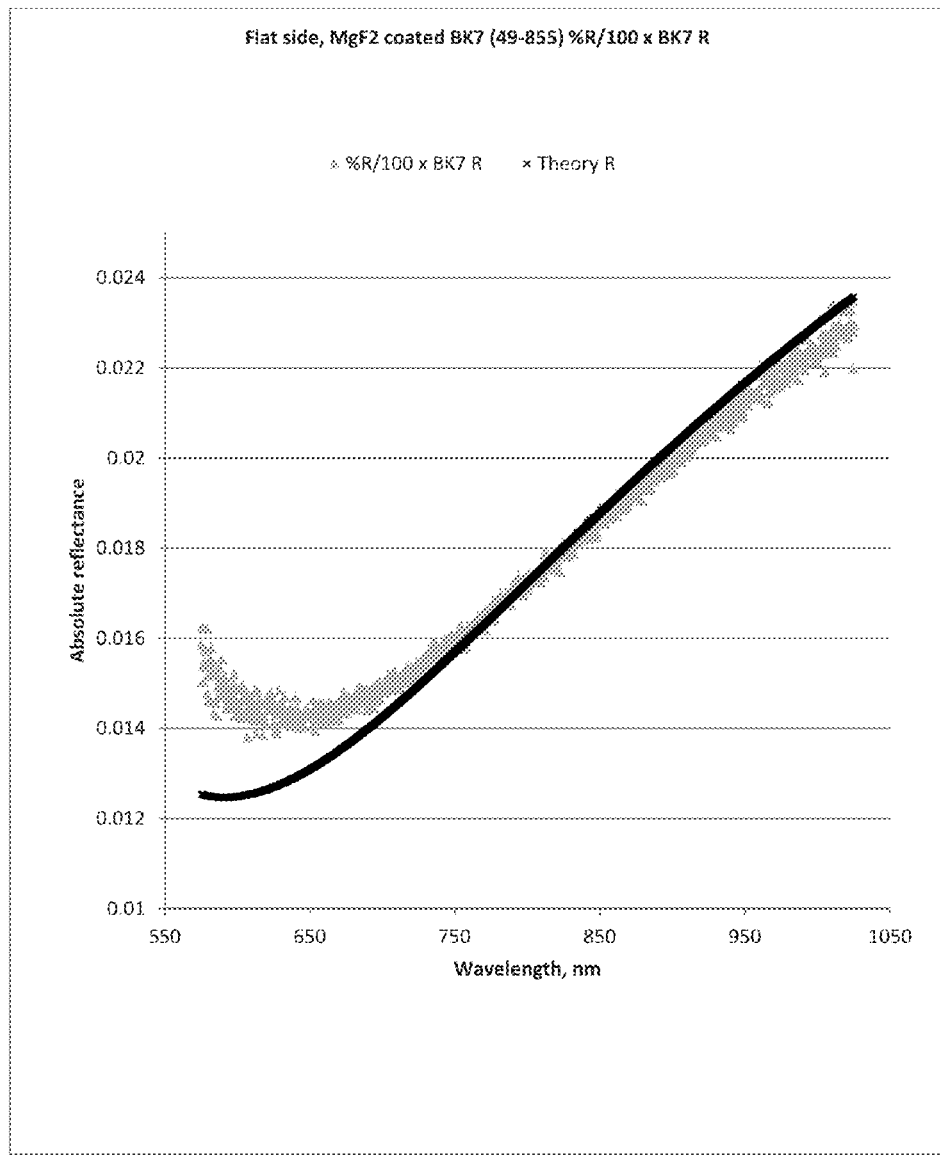

Given that the above results were obtained using the novel methods disclosed herein, there is potential uncertainty as to whether the $MgF_2$ film thickness is 111.98 nm. Thus, a more rigorous method confirmation experiment was conducted using a 12.7 mm diameter, 7.75 mm radius of curvature $MgF_2$-coated plano-convex BK7 lens (Edmunds part no. 49-855). Using the methods disclosed herein with an interferometer light source voltage of 5.5V, the $MgF_2$ coating thickness was measured on both sides. The convex side was measured using a 7.75 mm radius of curvature uncoated BK7 lens as reference and the b-term mathematics process was employed. The plano (flat) side was measured using a flat uncoated BK7 reference lens. The thickness calculations for flat samples do not always require the use of the b-term. The b-term is useful when employing flat references when the reference surface is not placed orthogonally to the incident light from the interferometer. Otherwise, the mathematics are identical to those used for curved surfaces. FIGS. 9 and 10 present the results. In FIG. 9, Dark triangles=% R/100×BK7 R; Light lines=Fitted R/(b=1.0585); and Dark x=Theory R. In FIG. 10, Light triangles=% R/100×BK7 R; and Dark x=Theory R.

The methods herein determined $MgF_2$ coating thicknesses to be 110.49 nm and 108.73 nm for the convex and flat sides, respectively. This is consistent with the assumption that the convex and flat surfaces were coated identically. As a further confirmation of the thickness of the $MgF_2$ coating, a spectroscopic Ellipsometer (model alpha SE, J. A. Woollam, Lincoln, Nebr. 68508-2243) was employed to measure thickness of the coating on the flat surface. However, the convex surface coating could not be measured with the ellipsometer due to beam geometry requiring flat samples. The ellipsometer measured a coating thickness for the flat surface of 110.0±0.64 nm, in excellent agreement with the interferometer result of 108.73 nm for this surface ($\Delta$ thickness=1.27 nm). Since ellipsometer measurements are considered correct within thin film technology hierarchy, and both the convex and flat surfaces are assumed to have identical coating thicknesses, the b-term method for thin films on curved surfaces has been additionally verified to have an error of only about 1 nm.

Figure 11:
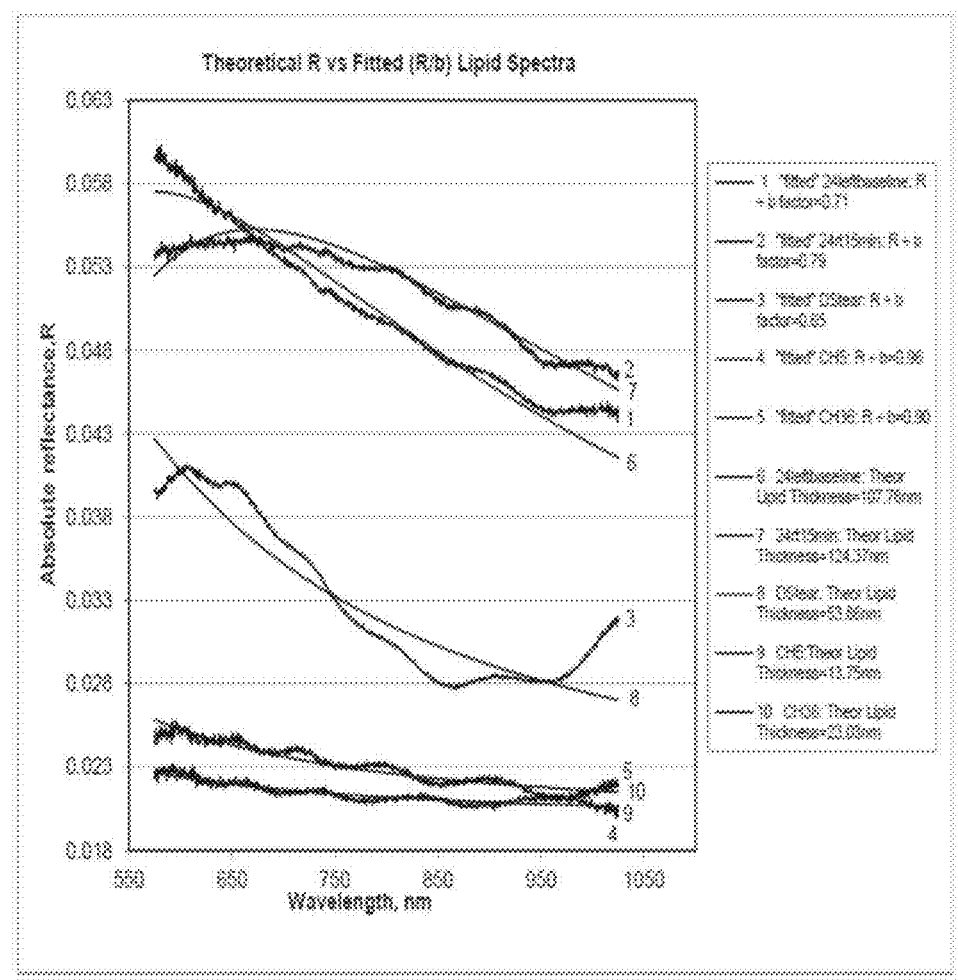
FIG. 11 shows calculated absolute reflectance spectra for tear film lipid spectra compared to calculated theoretical spectra.

Finally, the previously developed Statistica software program was applied to tear film lipid spectra, where the input data are $v5=R(\lambda)$ meas tear lipid sample×$R(\lambda)$ abs BK7 reference (BK7 abs R calc)/100 and where $v1=n_0$ air=1, $v2=n_1(\lambda)$ lipid, $v3=n_2(\lambda)$ aqueous, $v4$=measured $\lambda$, the variable 'a' is the fitted lipid film thickness, and the variable 'b' is the final correction term which moves the measured spectrum up or down on the theoretical R axis (y-axis) to achieve a match with theory (FIG. 11).

The measured spectra in FIG. 11 were plotted by dividing v5 by the fitted b-term at each wavelength. FIG. 11 shows lipid film thicknesses varying from 13.75 nm to 23.03 nm, 53.86 nm, 107.76 nm and 124.37 nm. It should be noted that the tear spectra in FIG. 11 include cosine-function oscillations from the aqueous layer (the smaller oscillations). These can be subtracted using a modified software program. Also, it is clear from the spectrum of the 188.6 nm SiO2 standard (not shown), that spectral data beyond 950-1000 nm may involve some optical error, perhaps from optical aberration. The spectrum of the 48.26 nm $SiO_2$ standard used with the curved BK7 reference in FIG. 7 also shows some optical error above 950-1000 nm. Thus, a refined software program may delete data beyond 950 nm. Nonetheless, it is seen that the lipid spectra match the theoretical spectra very well. Note, these spectra were acquired over 504 msec, to simultaneously measure the aqueous layer. It is known that the lipid layer thickness may change over this time interval. This can cause measured spectra such as the 53.86 nm spectrum to deviate somewhat from theory. In various embodiments, spectra will be acquired in intervals as short as 20-100 msec to resolve this question. Alternatively, the shape of the 53.86 nm spectrum may arise from lipid film thickness variation within the 133 um×12.5 um spot. In various embodiments, the spot size will be reduced to resolve this question.

A modified Statistica software program was created, using a series of input values, where the input data are v6-v155=R ($\lambda$) meas tear lipid samples and where $v1=n_0$ air=1, $v2=n_1(\lambda)$ lipid, $v3=n_2(\lambda)$ aqueous, $v4$=measured $\lambda$ and where $v5=R(\lambda)$ abs BK7 reference (BK7 abs R calc)/100 and where the variable a=the fitted lipid film thickness and the variable b=the final correction term which moves the measured spectrum up or down on the theoretical R axis (y-axis) to achieve a match with theory. Here the Euler equation becomes:

$$v6-v155=(1-((8*v1*v2**2*v3)/((v12+v22)*(v22+v32)+4*v1*v2**2*v3+((v12-v22)*(v22-v32)*(\cos(4*3.14159*v2*a*0.98666/v4))))))*b/v5.$$

Statistica software program code follows for the first several spectrum calculations (v6 and v7). Here, the starting value for lipid thickness=65 nm=a-term starting value. The b-term starting value is set to 0.66. Measured spectra wavelength is edited to 575-950 nm:

```
S1.DeleteCases 1, 30 and S1.DeleteCases 730, 994
Option Base 1
Sub Main
Dim AO As AnalysisOutput
Dim AWB As Workbook
Dim S1 As Spreadsheet
Set S1 = ActiveDataSet
S1.DeleteCases 1, 30
S1.DeleteCases 730, 994
```

```
Dim newanalysis2 As Analysis
Set newanalysis2 = Analysis (scNonlinearEstimation, S1)
With newanalysis2.Dialog
    .NonlinearMethod = scNlnUserSpecifiedRegressionLeastSquares
End With
newanalysis2.Run
With newanalysis2.Dialog
    .UserFunction = "v6 = ((1−
((8*v1*v2**2*v3)/((v1**2+v2**2)*(v2**2+v3**2)+4*v1*v2**2*v3+
((v1**2−v2**2)*(v2**2−v3**2)*(cos(4*3.14159*v2*a*0.98666/
v4)))))))*b/v5"
    .CasewiseDeletionOfMD = True
End With
newanalysis2.Run
With newanalysis2.Dialog
    .EstimationMethod = scNlnLevenbergMarquardt
    .MaxNumberOfIterations = 50
    .ConvergenceCriterion = 6
    .StartValues = "65 .66 "
End With
newanalysis2.Run
With newanalysis2.Dialog
    .AlphaForLimits = 95
    .PLevelForHighlighting = 0.05
End With
Set AO = newanalysis2.RouteOutput(newanalysis2.Dialog.Summary)
AO.Visible = True
If AO.HasWorkbook Then
        Set AWB = AO.Workbook
Else
        Set AWB = Nothing
End If
newanalysis2.GoBack
With newanalysis2.Dialog
    .UserFunction = "v7 = ((1−
((8*v1*v2**2*v3)/((v1**2+v2**2)*(v2**2+v3**2)+4*v1*v2**2*v3+
((v1**2−v2**2)*(v2**2−v3**2)*(cos(4*3.14159*v2*a*0.98666/
v4)))))))*b/v5"
    .CasewiseDeletionOfMD = True
End With
newanalysis2.Run
With newanalysis2.Dialog
    .EstimationMethod = scNlnLevenbergMarquardt
    .MaxNumberOfIterations = 50
    .ConvergenceCriterion = 6
    .StartValues = "65 .66 "
End With
newanalysis2.Run
With newanalysis2.Dialog
    .AlphaForLimits = 95
    .PLevelForHighlighting = 0.05
End With
Set AO = newanalysis2.RouteOutput(newanalysis2.Dialog.Summary)
AO.Visible = True
If AO.HasWorkbook Then
        Set AWB = AO.Workbook
Else
        Set AWB = Nothing
End If
```

The remaining program code follows the above repeating sequence for additional spectra calculations.

A sample portion of the v1-v6 inputs for a single spectrum (columns 1-6, left to right, where v6=measured % reflectance for tear lipid spectrum #1) follows in Table 4. Note these columns extend to the last measured wavelength (1085.11 nm, not shown), and the first 30 rows (shown as input data examples here) and rows where $\lambda \geq 950.6843$ nm are deleted by the software.

TABLE 4

| | | | | | |
|---|---|---|---|---|---|
| 1 | 1.48173057 | 1.33783826 | 559.409653 | 0.00042340272 | 36.8916 |
| 1 | 1.48165317 | 1.33782012 | 559.929243 | 0.000423370425 | 36.1339 |
| 1 | 1.48157604 | 1.33780203 | 560.448833 | 0.000423338215 | 36.167 |
| 1 | 1.48149916 | 1.33778399 | 560.968423 | 0.00042330609 | 36.2099 |
| 1 | 1.48142254 | 1.337766 | 561.488013 | 0.000423274049 | 36.5871 |
| 1 | 1.48134618 | 1.33774806 | 562.007604 | 0.000423242093 | 36.8416 |
| 1 | 1.48127008 | 1.33773018 | 562.527194 | 0.000423210221 | 36.2501 |
| 1 | 1.48119423 | 1.33771234 | 563.046784 | 0.000423178432 | 36.5386 |
| 1 | 1.48111863 | 1.33769455 | 563.566375 | 0.000423146727 | 35.974 |
| 1 | 1.48104329 | 1.33767681 | 564.085965 | 0.000423115104 | 35.8217 |
| 1 | 1.48096819 | 1.33765911 | 564.605555 | 0.000423083565 | 35.6451 |
| 1 | 1.48089335 | 1.33764147 | 565.125145 | 0.000423052107 | 35.7768 |
| 1 | 1.48081875 | 1.33762388 | 565.644736 | 0.000423020732 | 35.82 |
| 1 | 1.48074441 | 1.33760633 | 566.164326 | 0.000422989438 | 35.8625 |
| 1 | 1.48067031 | 1.33758883 | 566.683916 | 0.000422958225 | 35.8153 |
| 1 | 1.48059646 | 1.33757138 | 557.203506 | 0.000422927093 | 35.9704 |
| 1 | 1.48052285 | 1.33755398 | 557.723096 | 0.000422896042 | 35.9033 |
| 1 | 1.48044948 | 1.33753663 | 568.242687 | 0.000422865072 | 35.8368 |
| 1 | 1.48037636 | 1.33751932 | 568.762277 | 0.000422834181 | 35.5937 |
| 1 | 1.48030348 | 1.33750206 | 569.281867 | 0.00042280337 | 35.6052 |
| 1 | 1.48023084 | 1.33748485 | 569.801457 | 0.000422772638 | 35.6605 |
| 1 | 1.48015843 | 1.33746768 | 570.321048 | 0.000422741985 | 35.3016 |
| 1 | 1.48008627 | 1.33745056 | 570.840638 | 0.000422711411 | 35.7279 |
| 1 | 1.48001434 | 1.33743349 | 571.360228 | 0.000422680916 | 35.6287 |
| 1 | 1.4799428 | 1.3374165 | 571.878762 | 0.00042265056 | 35.2528 |
| 1 | 1.47987134 | 1.33739952 | 572.398352 | 0.00042262022 | 34.7073 |
| 1 | 1.47980012 | 1.33738259 | 572.917943 | 0.000422589957 | 35.3448 |
| 1 | 1.47972913 | 1.3373657 | 573.437533 | 0.000422559772 | 35.0115 |
| 1 | 1.47965838 | 1.33734886 | 573.957123 | 0.000422529664 | 35.5492 |

TABLE 4-continued

| | | | | |
|---|---|---|---|---|
| 1 | 1.47958785 | 1.33733207 | 574.476713 | 0.000422499632 | 35.069 |
| 1 | 1.4795177 | 1.33731535 | 574.995248 | 0.000422469737 | 35.1151 |
| 1 | 1.47944763 | 1.33729865 | 575.514838 | 0.000422439857 | 34.7243 |

Figure 12:
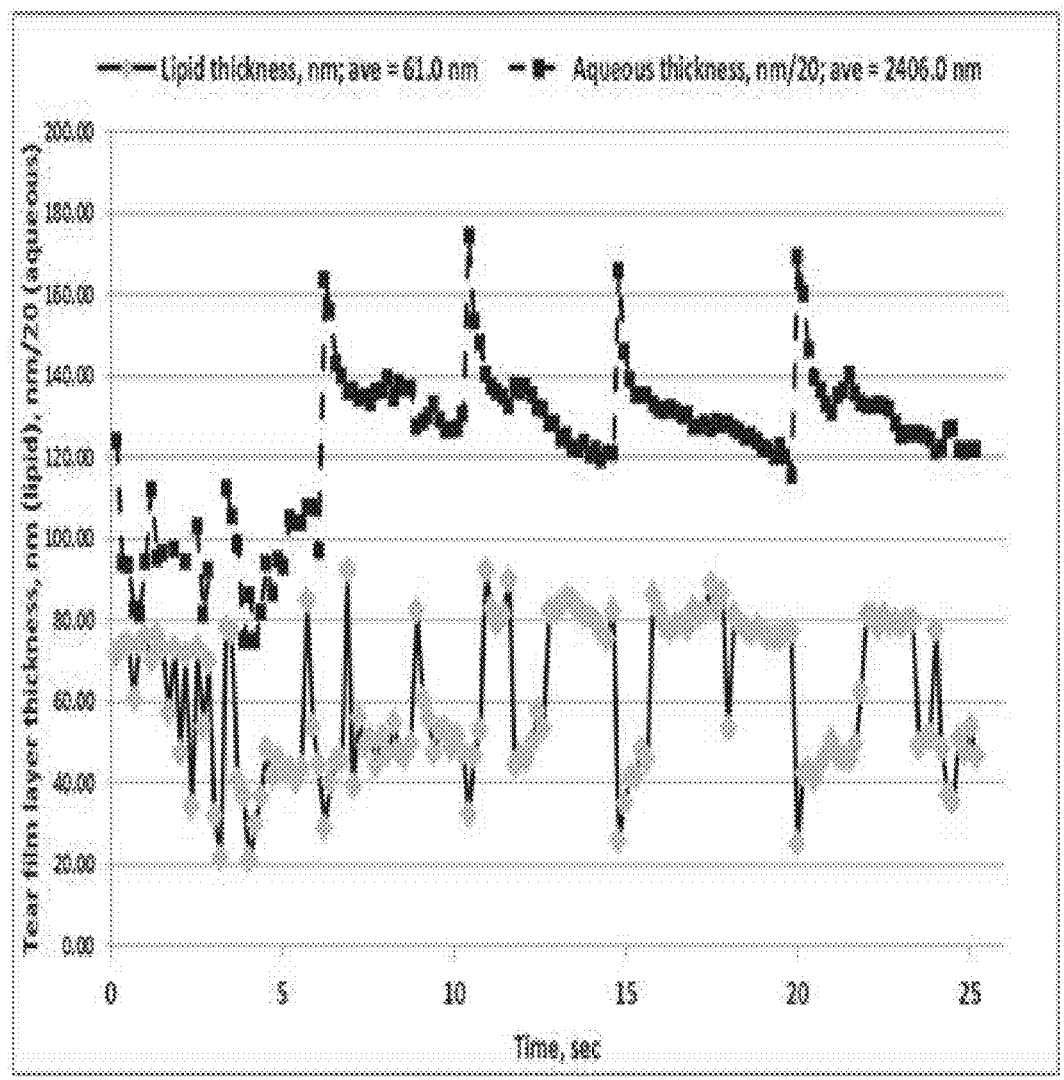
FIG. 12 shows thicknesses of the lipid (diamonds) vs. aqueous (squares) tear film layers during blinking (downward spikes in lipid thickness measurements) of the subject's eyelids.

FIG. 12 illustrates the results of using the lipid thickness method herein to measure tear lipid layer thickness 150× over a 25.2 second period. It was found that in a few cases, a 65 nm starting value for the a-term resulted in a correct, but negative value, for the thickness. In any case, such results occur infrequently. A test of the current method with these 150 spectra produced only 5 such results (3.3%), which is considered acceptable. It is not currently known why correct values with negative signs are observed. All of the negative-sign results observed thus far have occurred with lipid layer thickness values less than 39.45 nm, which are further away from the 65 nm starting value than many spectra. In any case, positive-value results are obtained for the aforementioned negative-value spectra by using a lower starting value for the a-term. Aqueous layer thickness and blinking were measured simultaneously according to known methods. Blinks are easily visualized by the spiking in the aqueous layer thickness at the same time as the blink. This technological capability to accurately and quickly measure the tear film lipid layer has not previously been demonstrated. The results show that the lipid layer averages 61.0 nm and thickens on average about 50 nm very quickly after a blink, within on average 0.588 seconds. These results are generally consistent with Korb, et. al, (Korb, D R, et. al. Tear Film Lipid Layer Thickness as a Function of Blinking. *Cornea* 13 (4):354-359. 1994), who showed that individuals with a lipid layer thickness of 75-150 nm demonstrated a mean increase in lipid layer thickness of 33 nm following forceful blinking They are also consistent with Goto, et. al, (Goto, E and Tseng, C G. Differentiation of Lipid Tear Deficiency Dry Eye by Kinetic Analysis of Tear Interference Images. *Arch Ophthalmol*. Vol. 121, February 2003, 173-180.), who showed that for those with 75 nm lipid films, mean lipid spread time following a blink was 0.36±0.22 seconds. FIG. 12 shows that contrary to one conventional theory, lipid layer thickening following a blink does not precede aqueous layer thickening. However, this is a single small test of the technology, and not a rigorous test of tear film spreading theory.

In various embodiments, the disclosed methods may be carried out on a computing system in communication with an interferometer (e.g. a wavelength-dependent interferometer). The computing system may include one or more computer systems in communication with one another through various wired and wireless communication means which may include communications through the Internet and/or a local network (LAN). Each computer system may include an input device, an output device, a storage medium (including non-transient computer-readable media), and a processor such as a microprocessor. Possible input devices include a keyboard, a computer mouse, a touch screen, and the like. Output devices include a cathode-ray tube (CRT) computer monitor, a LCD or LED computer monitor, and the like. Storage media may include various types of memory such as a hard disk, RAM, flash memory, and other magnetic, optical, physical, or electronic memory devices. The processor may be any suitable computer processor for performing calculations and directing other functions for performing input, output, calculation, and display of data in the disclosed system. Implementation of the computing system may include generating a set of instructions and data that are stored on one or more of the storage media and operated on by a controller. Thus, one or more controllers may be programmed to carry out embodiments of the disclosed invention. The data associated with the system may include image data, numerical data, or other types of data.

Novel mathematical algorithms and software methods have been independently developed to calculate absolute-reflectance of tear film lipid layers from measured tear film lipid layer reflectance using wavelength-dependent optical interferometry. The absolute reflectance measurements are used for the accurate and quick determination of lipid layer thickness. These algorithms are consistent with optical theory, with the exception of a single b-term, which may be empirically explained by light reflection from a curved surface or from non-orthogonal placement of a flat surface or from out-of-focus light reflection.

Thickness errors for the methods herein for thin films on curved surfaces in perfect focus are only a few nanometers (nm). In practice, collecting ≥50 tear lipid measurements, deleting out-of-focus spectra, and averaging the remaining spectra will keep lipid thickness errors small.

These methods are suitable for the quantitative evaluation of the effects of novel dual-function lipid-supplementation tear formulas on the tear film lipid layer. They are also useful for evaluating the effects of other eye drops, ophthalmic dry eye drugs and MPS solutions, and contact lenses on the tear film lipid layer.

Novel features of the present disclosure include the use of the expanded Euler equation with interferometer-dependent wavelength selection of wavelength-dependent Sellmaier equation-fitted complex refractive indices in the software program to calculate tear film lipid layer thickness, where v6, the measured reflectance variable R($\lambda$) in an expanded Euler equation, is known and the actual lipid thickness d becomes the fitted lipid film thickness variable "a" (e.g., variable reversal in the expanded Euler equation) and wherein the expanded Euler equation also has a variable b, which is the final correction term which mathematically adjusts measured reflectance R (moves the measured spectrum up or down on the theoretical R axis (y-axis)) to achieve a match with theory:

$$v6=(1-((8*v1*v2**2*v3)/((v12+v22)*(v22+v32)+4*v1*v2**2*v3+((v12-v22)*(v22-v32)*(\cos(4*3.14159*v2*a*0.98666/v4))))))*b/v5$$

where v1=$n_0$ air=1, v2=$n_1(\lambda)$ lipid (Sellmeier-form), v3=$n_2(\lambda)$ aqueous, v4=measured $\lambda$, and v5=R($\lambda$) abs BK7 reference (BK7 abs R calc)/100 and wherein a Levenberg-Marquardt algorithm is used with a novel software program and a starting value for the a-term of 65 nm and for the b-term between 0 and 1.30 so that the program achieves the correct thickness and wherein spectral data without optical aberration between 575-950 nm are most preferred.

Other novel features include a method wherein a tear film lipid spectrum and slope is evaluated and a tear lipid layer thickness is estimated and this thickness estimate is thereafter used as the starting value for the a-term in the method above.

The following non-limiting Examples are intended to be purely illustrative, and show specific experiments that were carried out in accordance with embodiments of the invention.

EXAMPLES

Example 1

Differential Reflection of Light of Varying Wavelengths by the Lipid Layer

Conventional thinking that the tear film lipid layer retards water evaporation from the aqueous layer of the tear film is now being questioned by several research groups. (See Fenner B J, Tong L. More to stable tears than thickness of the tear film lipid layer. Invest Ophthalmol Vis Sci. 2015; 56:1601; incorporated by reference herein in its entirety). Nevertheless, the tear film lipid layer unambiguously reflects light of different wavelengths differentially. Maximum lipid layer light reflection across the short wavelength spectrum encompassing UVB, UVA, violet and blue light wavelengths peaks at about a lipid layer thickness range of 50-80 nm. Excluding UVB wavelengths, which natural human lenses block, maximum lipid layer light reflection for the sum of three selected midpoint of range wavelengths representing UVA (360 nm), violet (420 nm) and blue (470 nm), peaks at about a lipid layer thickness of 66 nm. It is of interest to note that the tear film lipid layer has been reported to have an average thickness of about 74 nm, ±23 nm (sd), with a range of 34-119 nm (Huth S W et al. U.S. Pat. No. 8,602,557 B2, incorporated herein by reference in its entirety). Another group measured the lipid layer and found a mean value of 76 nm±25 nm, range 23-134 nm (Finis D et al. Evaluation of lipid layer thickness measurement of the tear film as a diagnostic tool for meibomian gland dysfunction. Cornea. 2013; 32(12): 1549-1553, incorporated herein by reference in its entirety). Fenner and Tong (2105) measured tear film lipid layer thickness and found an average of 64.9±23.5 nm. These thickness measurements coincide nicely with the maximum light reflectivity of the lipid layer across the short wavelength range. Even though lipid layer light reflectivity values are low (e.g. on average about 5% to 6% of the short wavelength light can be blocked by a 50-80 nm lipid layer), over several decades this may become biologically meaningful. This serves as the hypothetical biological rationale for methods of the present invention involving measurement of the tear film lipid layer and thereafter to recommend a light blocking IOL.

Several studies have implicated short-wavelength, e.g. UVB (290-320 nm), UVA (320-400 nm), violet (400-440 nm) and/or blue-light (440-500 nm) as risk factors for age-related macular degeneration following cataract surgery. Also, the natural human lens retards transmission of UVA, violet, blue and green light, with older lenses transmitting less light (Mainster M A. Violet and blue light blocking intraocular lenses: photoprotection versus photoreception. Br. J Ophthalmol. 2006 June; 90(6):784-792, incorporated herein by reference in its entirety). The aforementioned article from Mainster reviews the spectral transmission properties of various IOLs. In general, the light transmission across all wavelengths of various commercial IOLs decreases in the order: UV transmitting>reduced UV blocking>UV only blocking>violet blocking>blue blocking lenses. Reduced UV blocking lenses are not described in the Mainster reference. These are defined herein as a lens such as the Abbott Medical Optics Inc. (AMO) Tecnis® or Sensar® brand IOLs, which block part of the UV radiation. Examples of Tecnis® brand IOLs which block part of the UV radiation are the Tecnis® ZCB00, PCB00 and ZMB00 lenses. An example of the Sensar® brand IOL is the Sensar® AAB00 lens. These are distinguished from the AMO Tecnis® Optiblue lens, which is a violet blocking IOL, as described in the Mainster reference. Thus the Tecnis® brand name is used for both reduced UV blocking and violet blocking IOLs. Recommendations have been developed for either a UV transmitting or reduced UV, UV only, violet or blue-blocking intraocular lens (IOL) based upon interpretation of these studies. Nonetheless, the inventors are not aware of a personal ocular diagnostic test that is available to quantitatively assess relative posterior ocular light exposure at these wavelengths.

Thus, in various embodiments candidates for IOL implantation may be provided with ocular diagnostic information about their relative posterior ocular UVB, UVA, violet and blue light exposure derived from their personal ocular biological characteristics, to assess their relative need for an IOL that attenuates or blocks at least one wavelength of light corresponding to ultraviolet, violet, or blue light, in particular a UV transmitting, reduced UV blocking, UV only blocking, violet blocking or blue blocking IOL lens. Thus, instead of generating estimates of this shorter wavelength light exposure that are based upon environment and personal behavior, a quantitative measure of relative exposure can be provided as disclosed herein. In some embodiments, the quantitative measure of relative exposure which is provided using the methods and systems disclosed herein may be combined with estimates that are based upon environment and personal behavior. The quantitative measure is based upon a measurement of the UVB, UVA, violet and blue light reflectivity or transmission of the patient's tear film lipid layer, since UVB, UVA, violet and blue light reflectivity (and hence transmission, which is the inverse of reflectivity) of the tear film lipid layer are uniform and repeatable functions of lipid layer thickness.

Figure 13:
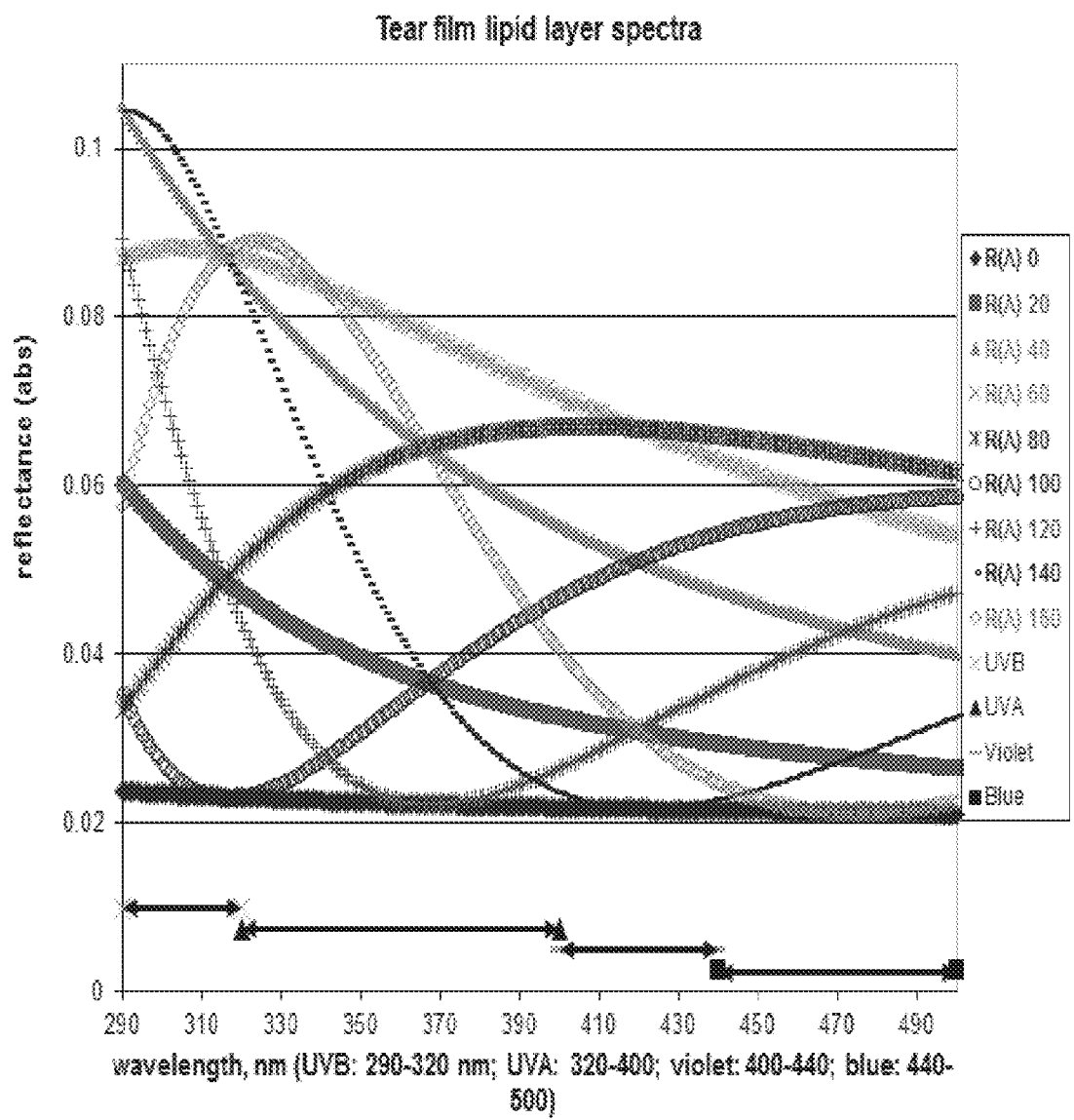
FIG. 13 shows tear film lipid layer reflectance vs. wavelength for varying tear film lipid layer thicknesses (in nm).
Figure 14:
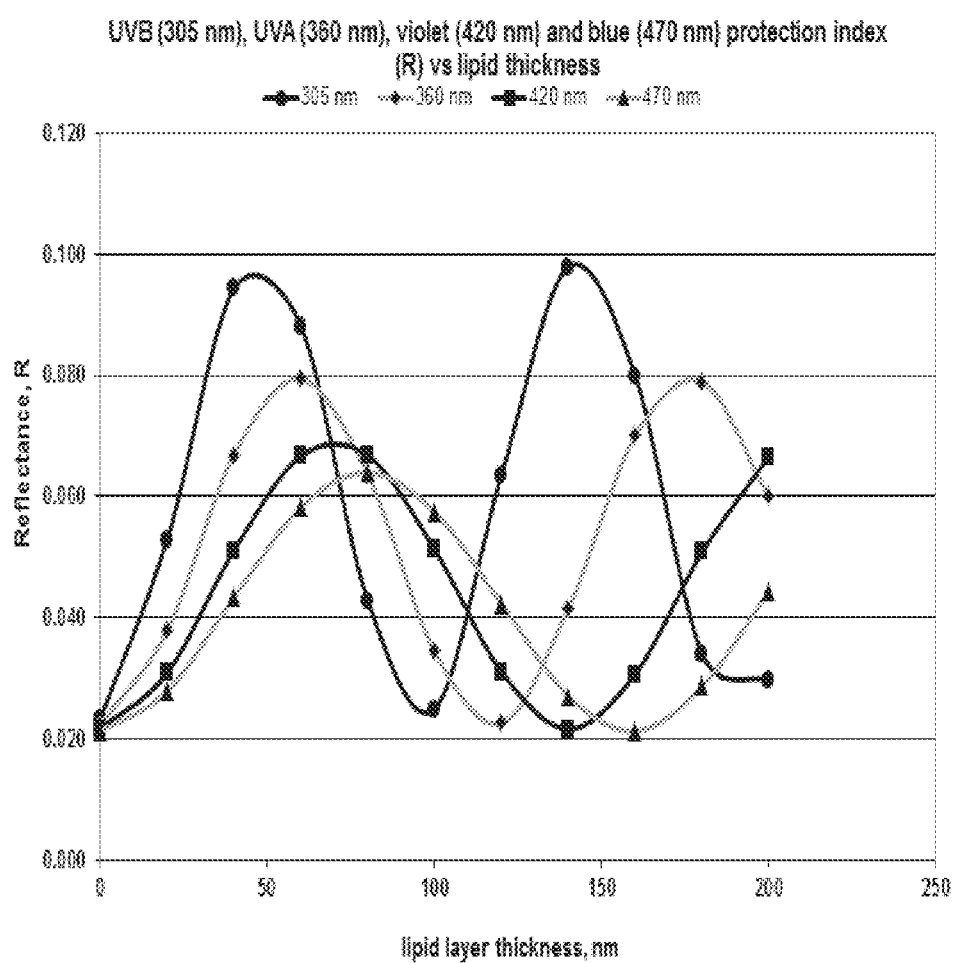
FIG. 14 shows the relationship between tear film lipid layer thickness and reflectance at UV-B (305 nm) and blue (410 nm) wavelengths, derived from the data in FIG. 13.

Accordingly, the methods of the present Example include the steps of (1) measuring tear film lipid layer thickness; (2) determining UVA and/or UVB and/or violet and/or blue light reflectivity or transmission of the lipid layer from a mathematical function which correlates lipid layer thickness to reflectivity or transmission; and (3) providing a recommendation for an IOL with a specific light transmission property. Using the methods disclosed herein, the tear film lipid layer thickness is determined for a given patient. This lipid layer thickness is then used to determine UVA and/or UVB and/or violet and/or blue light reflectivity or transmission as described below. FIG. 13 shows calculated tear film lipid layer absolute reflectance $R(\lambda)$ vs. wavelength for varying tear film lipid layer thicknesses in a wavelength range of 290-500 nm, which includes UV, violet and blue light. FIG. 14 shows the relationship between tear film lipid layer thickness and reflectance at UVB (e.g. about 305 nm; similar relationships can be constructed for wider ranges of UVB, e.g. about 300-310 nm or about 290-320 nm), UVA (e.g. about 360 nm; similar relationships can be constructed for wider ranges of UVA, e.g. about 340-380 nm, or 320-400 nm), violet (e.g., about 420 nm; similar relationships can be constructed for wider ranges of violet, e.g., about 410-430 nm, or 400-440 nm) and blue (e.g. about 470 nm; similar relationships can be constructed for wider ranges of blue, e.g. about 460-480 nm, or about 440-500 nm, derived from data such as that shown in FIG. 13.

From the data in FIG. 14, it can be seen that lipid layer reflectance at UVB, UVA, violet, and blue wavelengths is a sine function of lipid layer thickness. Further, from basic optical principles, light transmission is an inverse function of reflectance. In other words, transmission is higher when reflectance is lower and vice versa. Also, transmission+reflectance=100%, assuming light scattering=0. Thus, it is seen that tear film lipid layers of about 60 nm and about 180 nm thicknesses, which correspond to local maxima in the reflectance curve for 360 nm light, have maximal light reflectance and thus minimal light transmission into the eye at the UVA light wavelength of 360 nm. In contrast, individuals with lipid layer thicknesses of about 0 nm and about 120 nm, which correspond to local minima in the reflectance curve for 360 nm light, will have maximal UVA light transmission into the eye. Table 5 presents an example of how this information can be used in prescribing an IOL lens. Table 5 shows light reflection at various wavelengths vs. tear film lipid layer thickness, as well as the sum of light reflectance for the UVA+UVB wavelengths and the sum for 420 and 470 nm wavelengths. In various embodiments, reflectances at other wavelengths may be combined to provide additional information for prescribing an IOL lens. In certain embodiments, reflectance at a UVA wavelength and at a UVB wavelength can be added together to obtain a UV light sum and reflectance at a violet light wavelength and a blue light wavelength can be added together to obtain a visible light sum, and the UV light sum and the visible light sum can each be compared to reference values to identify an IOL for attenuating or blocking at least one wavelength of light corresponding to UV, violet, or blue light, as discussed further below.

TABLE 5

| Tear lipid t, nm | UVB (305 nm) | UVA (360 nm) | Violet (420 nm) | Blue (470 nm) | sum (UVA + UVB) | sum (420 + 470) |
|---|---|---|---|---|---|---|
| 0 | 0.023 | 0.022 | 0.022 | 0.021 | 0.046 | 0.043 |
| 20 | 0.053 | 0.038 | 0.031 | 0.028 | 0.091 | 0.059 |
| 40 | 0.094 | 0.067 | 0.051 | 0.043 | 0.161 | 0.094 |
| 60 | 0.088 | 0.079 | 0.067 | 0.058 | 0.168 | 0.125 |
| 80 | 0.043 | 0.064 | 0.067 | 0.064 | 0.106 | 0.131 |
| 100 | 0.025 | 0.034 | 0.051 | 0.058 | 0.059 | 0.109 |
| 120 | 0.064 | 0.023 | 0.031 | 0.042 | 0.086 | 0.073 |
| 140 | 0.098 | 0.042 | 0.022 | 0.027 | 0.139 | 0.049 |
| 160 | 0.080 | 0.070 | 0.031 | 0.021 | 0.150 | 0.052 |
| 180 | 0.034 | 0.079 | 0.051 | 0.029 | 0.113 | 0.080 |
| 200 | 0.030 | 0.060 | 0.067 | 0.044 | 0.090 | 0.111 |

An example of an algorithm to use to determine a prescription recommendation for a particular IOL is as follows: If the UVA+UVB sum is ≥0.106 and the 420+470 nm sum is simultaneously ≥0.0904, then a recommendation for either a UV transmitting or reduced UV blocking IOL may be given. This corresponds to measured tear film lipid layer thicknesses of 40, 60 or 80 nm or, more generally, any tear film lipid layer thickness between 40-80 nm. If the UVA+UVB sum is 0.059-0.106 and the 420+470 nm sum is simultaneously >0.0904, then a recommendation for a UV blocking IOL can be given. This corresponds to measured tear film lipid layer thicknesses of 40, 80-100 and 200 nm. If the 420 nm reflectance is <0.042 and the 470 nm reflectance is ≥0.042, then a recommendation for a violet blocking IOL can be given. This corresponds to measured tear film lipid layer thicknesses about 120 nm. If the 420+470 nm reflectance sum is between 0.043-0.094, then a recommendation for a blue blocking IOL can be given. This corresponds to measured tear film lipid layer thicknesses of from 0 to about 40 nm and about 120 to about 180 nm.

Thus, the foregoing example method involves first measuring the subject's tear film lipid layer thickness and, based on the thickness, thereafter determining the lipid layer reflectance at UVA (360 nm), UVB (305 nm), violet (420 nm) and blue (470 nm) light wavelengths, summing the reflectance values for UVA+UVB and also for 420+470 nm, and then following the algorithm above for IOL selection based upon the reflectance sums. Note that for some tear film lipid layer thicknesses, multiple options for IOLs may be recommended. In these cases, other factors can be taken under consideration in determining the IOL recommendation, such as the refractive vision needs of the patient. Thus, both safety and refractive vision needs can be taken under consideration simultaneously.

Table 6 summarizes the IOL recommendations for this example with reference to specific commercial IOLs. Note that specific commercial IOLs were selected based upon information provided in the Mainster reference, with the exception of the AMO reduced UV-blocking Tecnis®/Sensar® IOLs. Other IOLs with spectral transmission characteristics which are similar to or different from those in Table 6 can also be prescribed for implantation into the eye based upon the disclosed methods.

Other algorithms linking tear film lipid layer thickness and reflectivity to spectral transmission characteristics of IOLs can also be utilized. An example of a general approach is to select an IOL having light wavelength blocking characteristics that match in wavelength or range of wavelengths the single lowest tear film lipid layer reflectivity or reflectivity range for the subject's tear film lipid layer thickness. For example, from FIG. 14 it can be seen that for a tear film lipid layer thickness of 50 nm, light of 470 nm has the lowest reflectance level among the four wavelengths that are graphed and thus one approach would be to select an IOL that blocks 470 nm light.

Alternatively, if the subject's lipid layer thickness indicates low values of light reflectivity for one or more wavelength ranges, an IOL can be selected which blocks light wavelengths corresponding to the longest wavelengths of the aforementioned ranges, as such IOLs also naturally block light wavelengths at shorter wavelength values (e.g., blue blocking IOLs also block violet, UVA and UVB light; violet blocking IOLs also block shorter wavelengths but do not block blue light).

TABLE 6

| Tear lipid t, nm | IOL Recommendation |
|---|---|
| 0 | Blue blocking (e.g., Alcon AcrySof SN60AT: AN30) |
| 20 | Blue blocking (e.g., Alcon AcrySof SN60AT: AN30) |
| 40 | Blue blocking or UV transmitting or reduced UV-blocking |
| 60 | UV transmitting (e.g., Eyeonics Crystalens AT-45: EC20) or reduced UV-blocking (e.g., AMO Tecnis/Sensar) |
| 80 | UV only blocking (e.g., AMD Clariflex: AC20) or reduced UV-blocking (e.g., AMO Tecnis/Sensar) or UV transmitting |
| 100 | UV only blocking (e.g., AMO Clariflex: AC20) |
| 120 | Blue or violet blocking (e.g., AMO Optiblue: AV20 & AV30) |
| 140 | Blue blocking |
| 160 | Blue blocking |
| 180 | Blue blocking |
| 200 | UV only blocking (e.g., AMO Clariflex: AC20) |

In various embodiments, reflectance may be determined for other wavelengths of light in the UV-violet-blue range (e.g. from about 290-500 nm) and used in conjunction with the diagnostic and treatment procedures disclosed herein. In some embodiments, certain tear film lipid layer thicknesses (or ranges of thicknesses) are identified at particular wavelengths as corresponding to local reflectance minima or maxima and thus diagnoses and treatments may be made based on the tear film lipid layer thickness alone without requiring an intervening step of determining the reflectance or transmission values.

In certain embodiments, the methods disclosed herein may be used to assess a patient's relative UV-violet-blue range (e.g. from about 290-500 nm) exposure in advance of cortical cataract formation. In such embodiments, a thickness of the patient's tear film lipid layer is determined and, using the methods described above and referring to a graph such as that shown in FIG. 14, the amount of UV-violet-blue range exposure may be determined based at least in part on the level of UV-violet-blue range reflectance/transmission for the patient.

In further embodiments, measurement of the patient's tear film lipid layer and determination of the amount of reflectance/transmission at a given wavelength (e.g. UVA/360 nm or blue light/470 nm) may be followed by administration (e.g. topical application) of an ophthalmic composition to alter light reflectance of the tear film lipid layer to improve one or more properties, for example to reduce transmission of light of undesirable wavelengths such as UVA, UVB, violet, or blue light. Topical application of ophthalmic compositions may be used to change properties of the lipid layer, for example to thicken the lipid layer, or the compositions may be applied to block or reduce transmission of light of particular wavelengths or ranges of wavelengths. An example of a type of ophthalmic composition which can be used to thicken the tear film lipid layer is an oil-in-water emulsion-based artificial tear. Examples of the latter are disclosed in WO 2011/068955 A1 and US 2013/0197083 A1, both of which are incorporated herein by reference in their entirety.

In still other embodiments, measurement of the patient's tear film lipid layer and determination of the amount of reflectance/transmission at a given wavelength (e.g. UVA/360 nm or blue light/470 nm) may be followed by a determination and recommendation of eyewear (e.g. contact lenses or glasses) with particular light transmission/blocking properties. For example, yellow-tinted sunglasses (which reduce or block blue light) may be recommended for an individual with a measured lipid layer thickness which maximizes blue light transmission. See, for example, the Mainster reference discussed above as well as Marmor (Marmor M F. Double fault! Ocular hazards of a tennis sunglass. Arch Ophthalmol 2001; 119: 1064-1066), which discloses that sunglasses typically block 93% of violet light (400-440 nm) and 88% of blue light (440-500 nm). In various embodiments, contact lenses with light-blocking properties can also be prescribed.

In other embodiments, one or more of the treatments above, including implantation of light-blocking IOLs, application of ophthalmic compositions, and use of particular eyewear, may be used in combination with one another.

Example 2

Use of Standard Error to Determine Goodness of Fit and Quality of Lipid Layer Thickness Estimate In some implementations of the Levenburg-Marquardt fitting algorithm employed in the presently-disclosed methods for determining tear film lipid layer thickness, less accurate or even incorrect results associated with a local, as opposed to a global, minimum in the least squares sum may be generated when an improper starting thickness value is used to start the iterative fitting procedure of the algorithm. Therefore, to determine lipid layer thickness there is a need to distinguish the more accurate or correct thickness results from those produced from poor fits. This Example describes using the standard error associated with the tear film lipid layer result to determine the goodness of fit and thus the reliability of the thickness result. We have observed that a low standard error corresponds to a better fit between the calculated absolute reflectance of the measured spectrum and the model theoretical absolute lipid reflectance spectrum. Thus by selecting values with low standard error, one can distinguish which thickness results are derived from better fits.

Three $SiO_2$ thin film standards calibrated to within 0.1-0.01 nm thickness by NIST (VLSI Standards, Inc. San Jose, Calif. 95134-2006) were used to validate this new procedure. Each standard was measured with a wavelength-dependent optical interferometer, and the resulting relative reflectance spectrum was converted to a calculated absolute reflectance spectrum by dividing by 100 and then multiplying by the absolute Si reference reflectance. The Statistica (StatSoft®, Tulsa, Okla.) software program employed in the present invention was then used to fit the calculated absolute reflectance spectrum to the equation below to obtain an estimated thickness value. Various input thickness values, denoted as variable a, were used to generate the results shown in Table 7 for all three $SiO_2$ standards. It was discovered that the correct thickness value was obtained only when the associated standard error was below 0.1. All the incorrect results had standard errors much greater than 0.1. This was surprising, as the standard error in this software program is close to and essentially $2\sigma$ of the mean result. Thus, for thin films on the order of 20-200 nm thickness, for example the $SiO_2$ thin film standard at 95.01 nm thickness, a $\sigma$ value of 0.7691 does not appear to be large enough to be significant. However, this error was associated with a thickness result of 323.99 nm for this 95.01 nm standard, a difference error of 228.98 nm. Therefore, the role of the standard error in this software program in the reliability of the result is not evident without the rigorous analysis herein.

The expanded Euler equation for use in the Statistica program is repeated from above:

$$V5 = (1-((8*v1*v2**2*v3)/((v12+v22)* (v22+v32)+4*v1*v2**2*v3+ ((v12-v22)*(v22-v32)*(\cos (4*3.14159*v2*a*0.98666/v4))))))*b$$

where v5=R(λ) SiO2 measured sample×R(λ) abs Si reference (Si abs R calculated)/100 and where v1=$n_0$ air=1, v2=$n_1$(λ) SiO2, v3=$n_2$(λ) Si, v4=measured λ, and the variable a, the fitted film thickness, and the variable b, the final correction term which moves the measured spectrum up or down on the theoretical R axis (y-axis) to achieve a match with theory.

TABLE 7

| Actual SiO$_2$ Thickness (nm) | Starting Input for "a" | Measured SiO$_2$ Thickness (nm) (Final "a" value) | Standard error | Input for b | b estimate |
|---|---|---|---|---|---|
| 48.26 | 50 | 47.57 | 0.0201 | 0.66 | 1.03 |
|  | 65 | 47.57 | 0.0201 | 0.66 | 1.03 |
|  | 100 | 47.57 | 0.0201 | 0.66 | 1.03 |
|  | 150 | 121.29 | 0.3843 | 0.66 | 2.67 |
|  | 200 | 269.48 | 0.6967 | 0.66 | 0.98 |
| 95.01 | 50 | 98.54 | 0.0487 | 0.66 | 1.06 |
|  | 65 | 98.54 | 0.0487 | 0.66 | 1.06 |
|  | 100 | 98.54 | 0.0487 | 0.66 | 1.06 |
|  | 200 | 323.99 | 0.7691 | 0.66 | 0.59 |
|  | 250 | 323.99 | 0.7691 | 0.66 | 0.59 |
| 188.58 | 125 | 190.53 | 0.0525 | 0.66 | 1.03 |
|  | 150 | 190.53 | 0.0525 | 0.66 | 1.03 |
|  | 200 | 190.53 | 0.0525 | 0.66 | 1.03 |
|  | 300 | 190.53 | 0.0525 | 0.66 | 1.03 |
|  | 350 | 458.77 | 0.8485 | 0.66 | 0.96 |

The method of using the standard error to evaluate thickness results can be applied to tear film lipid spectra. Interferometric reflectance spectra of a human subject's right eye tear film were collected, as described in U.S. Pat. No. 7,963,655 B2 (incorporated by reference herein in its entirety) and processed with the modified Statistica program where the input data ranges are $v6-v155=R(\lambda)$ meas tear lipid samples and where $v1=n_0$ air=1, $v2=n_1(\lambda)$ lipid, $v3=n_2(\lambda)$ aqueous, $v4$=measured $\lambda$ and where $v5=R(\lambda)$ abs BK7 reference (BK7 abs R calc)/100 and where the variable a=the fitted lipid film thickness and the variable b=the final correction term which moves the measured spectrum up or down on the theoretical R axis (y-axis) to achieve a match with theory. Here the Euler equation becomes:

$$v6-v155=(1-((8*v1*v2**2*v3)/((v12+v22)*(v22+v32)+4*v1*v2**2*v3+((v12-v22)*(v22-v32)*(\cos(4*3.14159*v2*a*0.98666/v4))))))*b/v5$$

Figure 15:
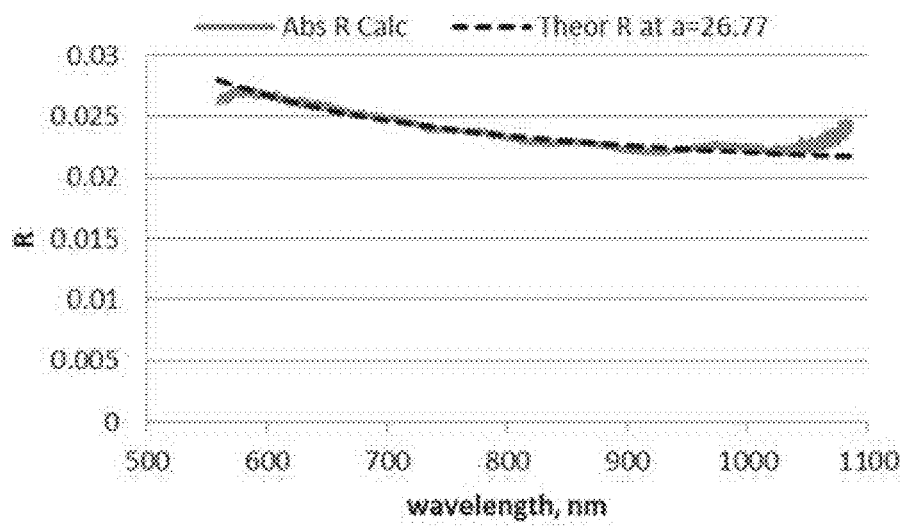
FIG. 15 shows the absolute calculated reflectance spectrum (solid grey line) compared to the theoretical reflectance spectrum (dashed lines) for a lipid thickness of 26.77 nm.
Figure 16:
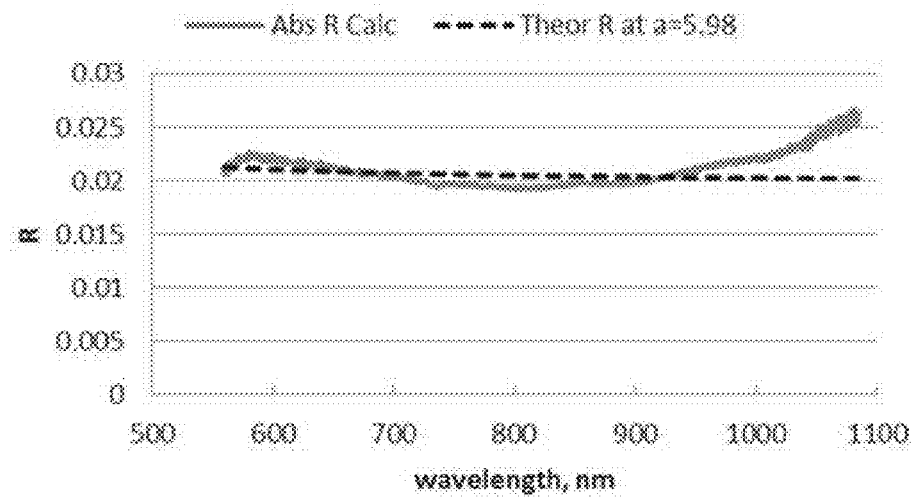
FIG. 16 shows the absolute calculated reflectance spectrum (solid grey line) compared to the theoretical reflectance spectrum (dashed lines) for a lipid thickness of 5.98 nm.

It can be seen that for lipid thickness values with a low standard error, as illustrated by RR Baseline#48, the absolute calculated reflectance spectrum (solid grey line, FIG. 15) closely matches the theoretical reflectance spectrum (dashed lines, FIG. 15). On the other hand, for thickness values with a high standard error, represented by RR Baseline#50, the fit between the absolute calculated reflectance and the theoretical reflectance is poor (FIG. 16). Thus the validity of the estimated thickness value, as seen by how well the measured spectrum fits to the theoretical spectrum, can be indicated by the size of the standard error.

Figure 17:
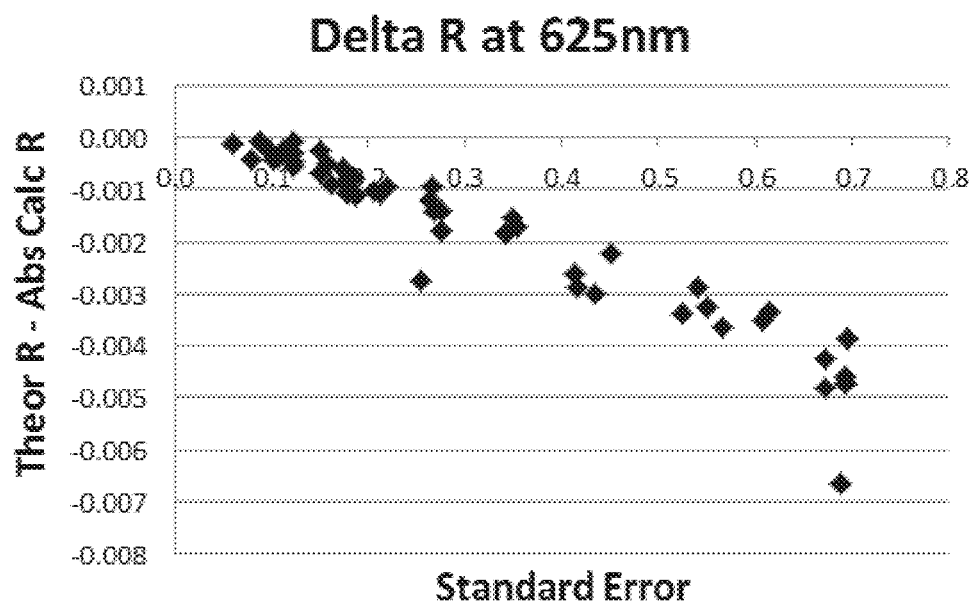
FIG. 17 shows the standard error associated with the lipid layer thicknesses of 50 tear film spectra is plotted against the difference between the theoretical reflectance and the absolute calculated reflectance (denoted as Delta R) at 625 nm.
Figure 18:
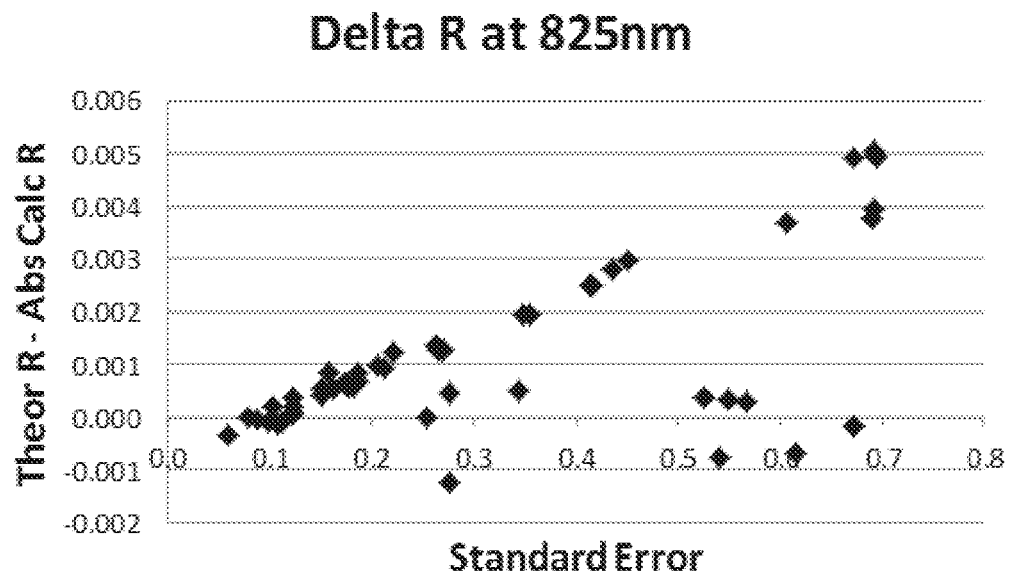
FIG. 18 shows the standard error associated with the lipid layer thicknesses of 50 tear film spectra is plotted against the difference between the theoretical reflectance and the absolute calculated reflectance (denoted as Delta R) at 825 nm.
Figure 19:
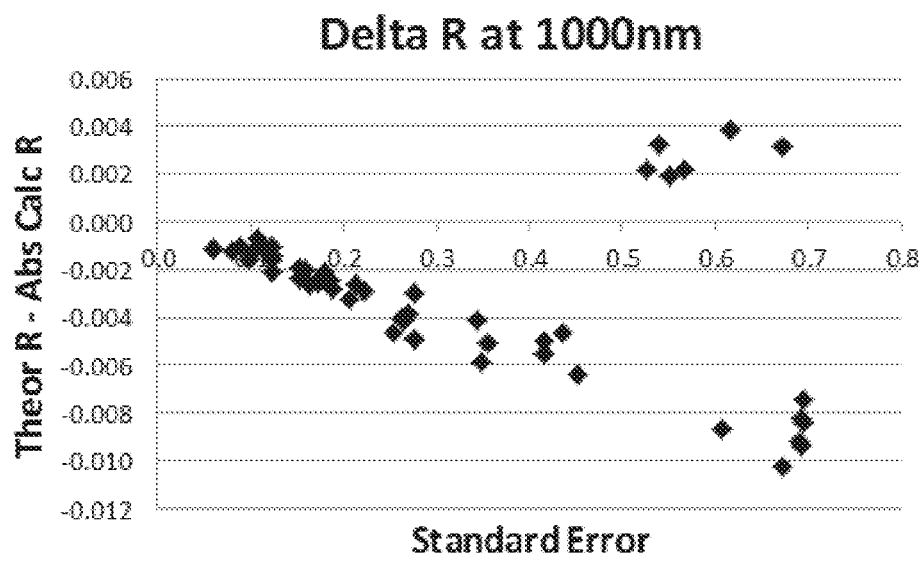
FIG. 19 shows the standard error associated with the lipid layer thicknesses of 50 tear film spectra is plotted against the difference between the theoretical reflectance and the absolute calculated reflectance (denoted as Delta R) at 1000 nm.

To further illustrate this point, the standard error associated with the lipid layer thicknesses of 50 tear film spectra is plotted against the difference between the theoretical reflectance and the absolute calculated reflectance (denoted as Delta R) at 625 nm, 825 nm, and 1000 nm (FIGS. 17-19) near the ends (625, 1000 nm) and middle (825 nm) of the spectra. As seen in FIGS. 17-19, as Delta R approaches zero, the standard error approaches 0.1 or less at the three representative wavelengths presented. Note in FIGS. 18 and 19 that Delta R values can approach 0 from both above and below the Delta R=0 axis. Note also that since FIG. 18 presents data at 825 nm near the center of the wavelength range, and that the Levenburg-Marquardt fitting algorithm is essentially comparing a theoretical slope line to a measured slope line wherein the centers of the lines near 825 nm often coincide in a "fulcrum-like" manner, low 825 nm Delta R values can be obtained with high standard errors because the plotted standard errors are derived from all wavelengths rather than just 825 nm. Overall, because low standard error occurs only when the difference between the complete measured and theoretical spectra (delta R) is low, one can use low standard error as a way to select more reliable thickness results.

A related method of the present invention involves determining the lipid layer thickness from the extracted lipid contribution of a measured spectrum. An interferometric reflectance spectrum of a human subject's tear film was taken, as described in U.S. Pat. No. 7,963,655 B2. The measured reflectance data was then fit to the following equation (Equation 1) where v2=measured reflectance, v1=wavelength, d=R0=(Rmax+Rmin)/2 where R=reflectance, e/2d=amplitude=(Rmax−Rmin)/(Rmax+Rmin), nd=refractive index of film, g=thickness of the aqueous+lipid layer, h=phase, the a, b, and c terms represent a 2nd order polynomial used to fit the raw data to the large slope oscillation caused by the lipid layer and the Exp(−j/(v1)2) term corrects for the modulation of fringe amplitude with wavelength.

$$v2=-a-b*v1-c*v1**2+d*(1+(e/2*d)*\cos((16.745*g/v1)+h))*\text{Exp}(-J/v1**2)$$

Equation 1:

The lipid contribution was then extracted out by taking the polynomial portion and Exp(−J/v1**2) term from the fitted equation above to form Equation 2. The Statistica software program employed in the present invention to calculate lipid layer thickness was then applied to a set of reflectance vs. wavelength data derived from the lipid contribution Equation 2 to determine the lipid layer thickness.

$$v2=-a-b*v1-c*v1**2+d*\text{Exp}(-J/v1**2)$$

Equation 2:

This method was performed on a tear film spectrum which was fit to Equation 1 to obtain the following equation below:

$$y=-(4.1861)-(0.006799)*x-(-0.33e-5)*x**2+1.18619*(1+((-0.59965)/2*(1.18619))*\cos((16.745*(1572.15)/x)+(-2.9802)))*\exp(-(498700/x**2))$$

Figure 20:
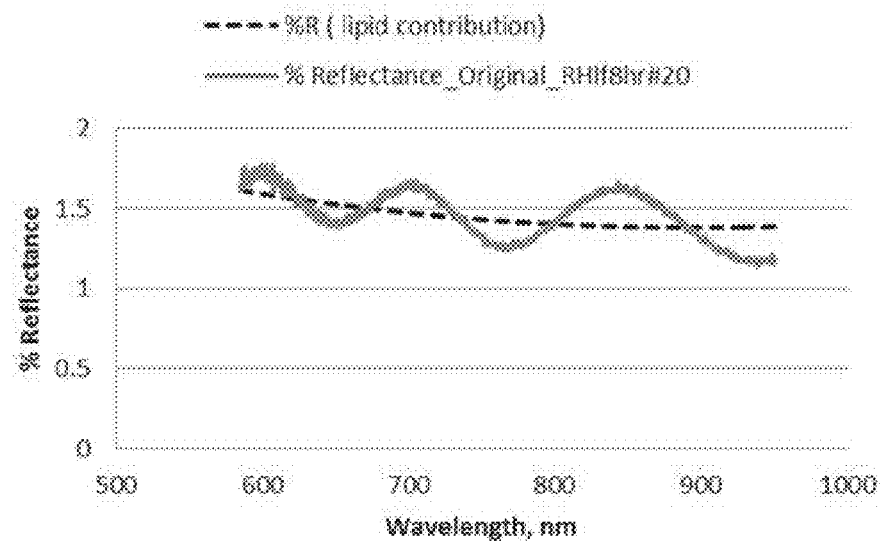
FIG. 20 shows the lipid-only reflectance spectrum (dashed lines) graphed with the original measured reflectance spectrum (solid gray line).

The lipid contribution equation then becomes $y=-(4.1861)-(0.006799)*x-(-0.33e-5)*x**2+1.18619*\exp(-(498700/x**2))$. When the lipid layer thickness was calculated for the original spectrum and secondly for the lipid-only spectrum, the standard error of the lipid only spectrum was much lower than the standard error of the original spectrum. The original spectrum had an estimated lipid thickness value of 31.5 nm with a relatively high standard error of 1.2, while the lipid spectrum had a thickness value of 26.5 nm and a much lower standard error of 0.09 (Table 8). As seen when the lipid-only reflectance spectrum (dashed lines) was graphed with the original measured reflectance spectrum in FIG. 20, the aqueous oscillations are absent from the lipid spectrum. It is surmised that aqueous oscillations may obscure the calculation of the lipid layer thickness and thereby produce a lipid thickness result with a higher standard error. Thus the application of this method of using the lipid contribution from a tear film spectrum will help lower the standard error of the lipid layer estimate.

TABLE 8

|  | Original Spectrum | Lipid Spectrum |
|---|---|---|
| Lipid Layer Thickness, nm | 31.49552 | 26.54374 |
| Standard error | 1.227539 | 0.091551 |

Accordingly, in various embodiments the method of determining a tear film lipid layer thickness includes measuring a tear film aqueous plus lipid layer relative reflectance spectrum using a wavelength-dependent optical interferometer; converting the measured tear film aqueous plus lipid layer relative reflectance spectrum to a calculated absolute reflectance spectrum; iteratively comparing the calculated absolute reflectance spectrum to a plurality of theoretical absolute reflectance lipid spectra to determine a tear film lipid layer thickness estimate; determining a standard error for the tear film lipid layer thickness estimate; and identifying a correct lipid layer thickness based on the standard error.

In certain embodiments a starting value is used for the variable 'a', the fitted film thickness. The Statistica software program then performs an iterative curve fitting as described previously, updating the 'a' value with each iteration e.g., 50 iterations or more). A standard error is determined for the various fitted film thickness estimates and, in general, the correct lipid layer thickness is identified based on when the standard error value is minimized. In some embodiments, a standard error of 0.1 or less indicates that the estimated thickness value is accurate, while a standard error of greater than 0.1 indicates that the estimated thickness value is less accurate or even inaccurate (e.g. see Table 7).

In some embodiments, when it is determined that the estimated thickness value is inaccurate, e.g. due to a standard error value being above 0.1, the iterative procedure may be restarted using a different starting value for the variable 'a.' As shown in Table 7, the choice of starting value for 'a' can influence the final estimated thickness estimate, i.e. the final value for 'a' after all of the iterations have been completed, and the standard error values provide a mechanism for identifying which are the correct final estimates.

REFERENCES

The following references are herein incorporated by reference in their entirety:

Scaffidi, R C, Korb, R. Comparison of the Efficacy of Two Lipid Emulsion Eyedrops in Increasing Tear Film Lipid Layer Thickness. Eye & Contact Lens: Science & Clinical Practice, 2007; 33(1):38-44.

Goto, et al. Computer-Synthesis of an Interference Color Chart of Human Tear Lipid Layer, by a Colorimetric Approach. Invest. Ophthalmol. Vis. Sci., 2003; 44:4693-4697.

Tiffany, J M. Refractive index of meibomian and other lipids. Current Eye Research, 5 (11), 1986, 887-889.

Stenzel, O. The Physics of Thin Film Optical Spectra. Editors: G. Ertl, H. Luth and D. Mills. Springer-Verlag Berlin Heidelberg 2005: 71-98.

Schott technical information document TIE-29 (2005).

Korb, D R, et. al. Tear Film Lipid Layer Thickness as a Function of Blinking Cornea 13 (4):354-359. 1994.

Goto, E and Tseng, C G. Differentiation of Lipid Tear Deficiency Dry Eye by Kinetic Analysis of Tear Interference Images. Arch Ophthalmol. Vol. 121, February 2003, 173-180.

Various features and advantages of the invention are set forth in the following claims.

What is claimed is:

1. A method for determining reflectivity of a tear film lipid layer of a patient, comprising the steps of:
measuring a tear film aqueous plus lipid layer relative reflectance spectrum using a wavelength-dependent optical interferometer;
converting the measured tear film aqueous plus lipid layer relative reflectance spectrum to a calculated absolute reflectance spectrum;
comparing the calculated absolute reflectance spectrum to a theoretical absolute lipid reflectance spectrum to determine a tear film lipid layer thickness; and
determining a reflectivity value for the tear film lipid layer thickness at a first wavelength of light corresponding to ultraviolet, violet, or blue light.

2. The method of claim 1, wherein the first wavelength of light corresponds to UVA light, and wherein the method further comprises
determining a reflectivity value for the tear film lipid layer thickness at a second wavelength of light corresponding to UVB light, a third wavelength of light corresponding to violet light, and a fourth wavelength of light corresponding to blue light,
adding together the reflectivity values for the first and second wavelengths to produce a UV light sum,
adding together the reflectivity values for the third and fourth wavelengths to produce a visible light sum, and
comparing the UV light sum and the visible light sum to reference values to identify an intraocular lens for attenuating or blocking at least one wavelength of light corresponding to ultraviolet, violet, or blue light.

3. The method of claim 2, wherein the first wavelength of light is within the range of 320-400 nm, the second wavelength of light is within the range of 290-320 nm, the third wavelength of light is within the range of 400-440 nm, and the fourth wavelength of light is within the range of 440-500 nm.

4. The method of claim 1, further comprising determining whether to provide a blue-blocking intraocular lens to the patient based on the reflectivity value.

5. The method of claim 4, wherein if the tear film lipid layer thickness is between 0-10 nm or between 130-150 nm then the patient is provided with a blue-blocking intraocular lens.

6. The method of claim 1, wherein the calculated absolute reflectance spectrum is calculated based on wavelength-dependent refractive indices for air, lipid, and aqueous phases and wherein the wavelength-dependent refractive indices for lipid are based upon a Sellmeier equation form.

7. The method of claim 1, wherein the tear film aqueous plus lipid layer relative reflectance spectrum is measured relative to a reference material.

8. The method of claim 1, wherein converting the measured tear film aqueous plus lipid layer relative reflectance spectrum to a calculated absolute reflectance spectrum comprises multiplying the measured tear film aqueous plus lipid layer relative reflectance spectrum at a plurality of wavelengths times an absolute reference spectrum for the reference material obtained at the plurality of wavelengths.

9. The method of claim 8, wherein converting the measured tear film aqueous plus lipid layer relative reflectance spectrum to a calculated absolute reflectance lipid spectrum further comprises dividing by a correction factor to correct for differences between the theoretical absolute reflectance spectrum and the calculated absolute reflectance spectrum.

10. The method of claim 8, wherein converting the measured tear film aqueous plus lipid layer relative reflectance spectrum to a calculated absolute lipid reflectance spectrum further comprises dividing by 100.

11. The method of claim 1, wherein comparing the calculated absolute reflectance spectrum to a theoretical absolute reflectance lipid spectrum comprises iteratively comparing the calculated absolute reflectance spectrum to a plurality of theoretical absolute reflectance lipid spectra.

12. The method of claim 11, wherein iteratively comparing the calculated absolute reflectance spectrum to a plurality of theoretical absolute reflectance lipid spectra comprises minimizing a sum of least squares differences between the calculated absolute reflectance spectrum and the theoretical absolute reflectance lipid spectra.

13. The method of claim 12, wherein minimizing a sum of least squares differences comprises using a Levenburg-Marquardt algorithm.

14. The method of claim 11, wherein iteratively comparing the calculated absolute reflectance spectrum to a plurality of theoretical absolute reflectance lipid spectra comprises starting the iteration with a theoretical absolute reflectance lipid spectrum for a 65 nm thick lipid layer.

15. The method of claim 1, wherein comparing the calculated absolute reflectance spectrum to a theoretical absolute lipid reflectance spectrum does not include a comparison of the calculated absolute reflectance spectrum to a theoretical absolute aqueous reflectance spectrum to determine a tear film aqueous layer thickness and a comparison of the calculated absolute reflectance spectrum to a theoretical film stack to determine corneal surface refractive index.

16. The method of claim 1, further comprising determining whether to administer an ophthalmic composition to the patient based on the reflectivity value.

17. The method of claim 1, further comprising determining whether to prescribe eyewear with particular light transmission or light blocking properties based on the reflectivity value.

18. A system for determining reflectivity of a tear film lipid layer of a patient, comprising:
   a wavelength-dependent optical interferometer; and
   a controller in communication with the interferometer, the controller configured to
      measure a tear film aqueous plus lipid layer relative reflectance spectrum using the interferometer,
      convert the measured tear film aqueous plus lipid layer relative reflectance spectrum to a calculated absolute reflectance spectrum,
      compare the calculated absolute reflectance spectrum to a theoretical absolute lipid reflectance spectrum to determine a tear film lipid layer thickness, and
      determine a reflectivity value for the tear film lipid layer thickness at a first wavelength of light corresponding to ultraviolet, violet, or blue light.

19. The system of claim 18, wherein the first wavelength of light corresponds to UVA light, and wherein the controller is further configured to
   determine a reflectivity value for the tear film lipid layer thickness at a second wavelength of light corresponding to UVB light, a third wavelength of light corresponding to violet light, and a fourth wavelength of light corresponding to blue light,
   add together the reflectivity values for the first and second wavelengths to produce a UV light sum,
   add together the reflectivity values for the third and fourth wavelengths to produce a visible light sum, and
   compare the UV light sum and the visible light sum to reference values to identify an intraocular lens for attenuating or blocking at least one wavelength of light corresponding to ultraviolet, violet, or blue light.

20. The system of claim 19, wherein the first wavelength of light is within the range of 320-400 nm, the second wavelength of light is within the range of 290-320 nm, the third wavelength of light is within the range of 400-440 nm, and the fourth wavelength of light is within the range of 440-500 nm.

21. The system of claim 18, wherein the controller is further configured to determine whether the patient should be provided with a blue-blocking intraocular lens based on the reflectivity value.

22. The system of claim 21, wherein if the tear film lipid layer thickness is between 0-10 nm or between 130-150 nm then the patient is provided with a blue-blocking intraocular lens.

23. The system of claim 18, wherein the calculated absolute reflectance spectrum is calculated based on wavelength-dependent refractive indices for air, lipid, and aqueous phases and wherein the wavelength-dependent refractive indices for lipid are based upon a Sellmeier equation form.

24. The system of claim 18, wherein the tear film aqueous plus lipid layer relative reflectance spectrum is measured relative to a reference material.

25. The system of claim 18, wherein the controller, in order to convert the measured tear film aqueous plus lipid layer relative reflectance spectrum to a calculated absolute reflectance spectrum, is further configured to multiply the measured tear film aqueous plus lipid layer relative reflectance spectrum at a plurality of wavelengths times an absolute reference spectrum for the reference material obtained at the plurality of wavelengths.

26. The system of claim 25, wherein the controller, in order to convert the measured tear film aqueous plus lipid layer relative reflectance spectrum to a calculated absolute reflectance lipid spectrum, is further configured to divide by a correction factor to correct for differences between the theoretical absolute reflectance spectrum and the calculated absolute reflectance spectrum.

27. The system of claim 18, wherein the controller, in order to compare the calculated absolute reflectance spectrum to a theoretical absolute reflectance lipid spectrum, is further configured to iteratively compare the calculated absolute reflectance spectrum to a plurality of theoretical absolute reflectance lipid spectra.

28. The system of claim 27, wherein the controller, in order to iteratively compare the calculated absolute reflectance spectrum to a plurality of theoretical absolute reflectance lipid spectra, is further configured to minimize a sum of least squares differences between the calculated absolute reflectance spectrum and the theoretical absolute reflectance lipid spectra.

29. The system of claim 27, wherein the controller, in order to iteratively compare the calculated absolute reflectance spectrum to a plurality of theoretical absolute reflectance lipid spectra, is further configured to start the iteration with a theoretical absolute reflectance lipid spectrum for a 65 nm thick lipid layer.

30. The system of claim 18, wherein the controller, in order to compare the calculated absolute reflectance spectrum to a theoretical absolute lipid reflectance spectrum, is further configured not to include a comparison of the calculated absolute reflectance spectrum to a theoretical absolute aqueous reflectance spectrum to determine a tear film aqueous layer thickness and a comparison of the calculated absolute reflectance spectrum to a theoretical film stack to determine corneal surface refractive index.

31. The system of claim 18, wherein the controller is further configured to indicate whether to administer an ophthalmic composition to the patient based on the reflectivity value.

32. The system of claim 18, wherein the controller is further configured to indicate whether to prescribe eyewear with particular light transmission or light blocking properties based on the reflectivity value.

* * * * *